United States Patent
Rockne et al.

(10) Patent No.: US 11,862,319 B2
(45) Date of Patent: *Jan. 2, 2024

(54) WOUND MANAGEMENT AND TREATMENT USING COMPUTER VISION AND MACHINE LEARNING

(71) Applicant: MatrixCare, Inc., Bloomington, MN (US)

(72) Inventors: Jessica Rockne, Bloomington, MN (US); Vivek Kumar, Bloomington, MN (US); Adhiraj Ganpat Prajapati, Bloomington, MN (US); Robert Price, Bloomington, MN (US); Kedar Mangesh Kadam, Bloomington, MN (US); Timothy James Heeren, Bloomington, MN (US); Nitin Gandhi, Bloomington, MN (US); Coleen Patrice Danielson, Bloomington, MN (US)

(73) Assignee: MatrixCare, Inc., Bloomington, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/085,411

(22) Filed: Dec. 20, 2022

(65) Prior Publication Data

US 2023/0207095 A1    Jun. 29, 2023

Related U.S. Application Data

(63) Continuation of application No. 17/562,908, filed on Dec. 27, 2021, now Pat. No. 11,568,976.

(51) Int. Cl.
*G16H 20/30*    (2018.01)
*G16H 50/20*    (2018.01)

(52) U.S. Cl.
CPC .............. *G16H 20/30* (2018.01); *G16H 50/20* (2018.01)

(58) Field of Classification Search
CPC ............................... G16H 20/30; G16H 50/20
(Continued)

(56) References Cited

U.S. PATENT DOCUMENTS

2020/0126226 A1\*    4/2020    Adiri ...................... G06T 5/008
2020/0193597 A1\*    6/2020    Fan ....................... A61B 5/7275
(Continued)

OTHER PUBLICATIONS

Mombini et al., Design Of A Machine Learning System For Prediction Of Chronic Wound Management Decisions, 2020, DOI: 10.1007/978-3-030-64823-7 2 (Year: 2020).\*
(Continued)

*Primary Examiner* — Joy Chng
(74) *Attorney, Agent, or Firm* — Patterson + Sheridan, LLP

(57) ABSTRACT

Certain aspects of the present disclosure provide techniques for wound management and treatment. This includes determining characteristics of a wound for a patient based on an image of the wound, including detecting the characteristics based on analyzing the image using a first ML model. The techniques further include identifying patient medical data including characteristics relating to a medical history for the patient, and predicting a first care plan for the patient based on providing the characteristics of the wound and the patient medical data to a second ML model. The first care plan is configured to be used to treat the wound for the patient.

20 Claims, 14 Drawing Sheets

(58) Field of Classification Search
USPC .......................................................... 705/2–3
See application file for complete search history.

(56) References Cited

U.S. PATENT DOCUMENTS

2021/0142890 A1* 5/2021 Adiri ...................... G16H 50/20
2021/0290152 A1* 9/2021 Vogel ..................... G16H 40/67

OTHER PUBLICATIONS

Moura et al., Artificial intelligence in the management and treatment of burns: a systematic review, Burns & Trauma, vol. 9, 2021, tkab022, https://doi.org/10.1093/burnst/tkab022 (Year: 2021).*
PCT, Notification of Transmittal of The International Search Report and The Written Opinion of The International Searching Authority, or The Declaration for Application PCT/US2022/082068 dated Feb. 14, 2023.
Moura et al., "Artifical intelligence in the management and treatment of burns: a systematic review," Burns & Trauma, vol. 9, 2021, tkab022, http://doi.org/10.1093/burst/tkab022 (Year: 2021).
Digital Wound Care, "Swift Skin and Wound: How a Smartphone App is Revolutionizing Wound Care." Swift, Feb. 12, 2019, https://swiftmedical.com/swift-skin-wound-how-a-smartphone-app-is-revolutionizing-wound-care/.

* cited by examiner

US 11,862,319 B2

WOUND MANAGEMENT AND TREATMENT USING COMPUTER VISION AND MACHINE LEARNING

CROSS-REFERENCE TO RELATED APPLICATIONS

This application claims priority to U.S. patent application Ser. No. 17/562,908, filed Dec. 27, 2021, the contents of which are incorporated herein by reference in their entirety.

INTRODUCTION

Aspects of the present disclosure relate to artificial intelligence and healthcare, and more specifically, to improved wound management and treatment using computer vision and machine learning (ML).

Managing and treating wounds in a patient is a common healthcare goal. For example, a patient may sustain a wound, and may seek treatment for the wound in a healthcare facility, or the patient may sustain, or worsen, a wound while residing in a healthcare facility or receiving managed care in an outpatient facility. Managing and treating these wounds is difficult because different wounds can require different treatment and can take different amounts of time to heal, depending on characteristics of the wound and of the patient. Further, generating a care plan for treatment is typically done manually by a care provider. This requires in-person examination and assessment of the wound, and manual creation, or modification, of a care plan to treat the wound. But this approach is prone to inaccuracies, for example because of the potential for human error, and is inefficient, because it requires hands on assessment and care plan generation by a care provider.

SUMMARY

Certain embodiments provide a method. The method includes determining a plurality of characteristics of a wound for a patient based on an image of the wound, including: detecting the plurality of characteristics based on analyzing the image using a first machine learning (ML) model. The method further includes identifying patient medical data including a plurality of characteristics relating to a medical history for the patient. The method further includes predicting a first care plan for the patient based on providing the plurality of characteristics of the wound and the patient medical data to a second ML model. The first care plan is configured to be used to treat the wound for the patient.

Further embodiments provide an apparatus including a memory, and a hardware processor communicatively coupled to the memory, the hardware processor configured to perform operations. The operations include determining a plurality of characteristics of a wound for a patient based on an image of the wound, including: detecting the plurality of characteristics based on analyzing the image using a ML model. The operations further include identifying patient medical data including a plurality of characteristics relating to a medical history for the patient. The operations further include predicting a first care plan for the patient based on providing the plurality of characteristics of the wound and the patient medical data to a second ML model. The first care plan is configured to be used to treat the wound for the patient.

Further embodiments provide a non-transitory computer-readable medium including instructions that, when executed by a processor, cause the processor to perform operations. The operations include determining a plurality of characteristics of a wound for a patient based on an image of the wound, including: detecting the plurality of characteristics based on analyzing the image using a ML model. The operations further include identifying patient medical data including a plurality of characteristics relating to a medical history for the patient. The operations further include predicting a first care plan for the patient based on providing the plurality of characteristics of the wound and the patient medical data to a second ML model. The first care plan is configured to be used to treat the wound for the patient.

The following description and the related drawings set forth in detail certain illustrative features of one or more embodiments.

DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1:
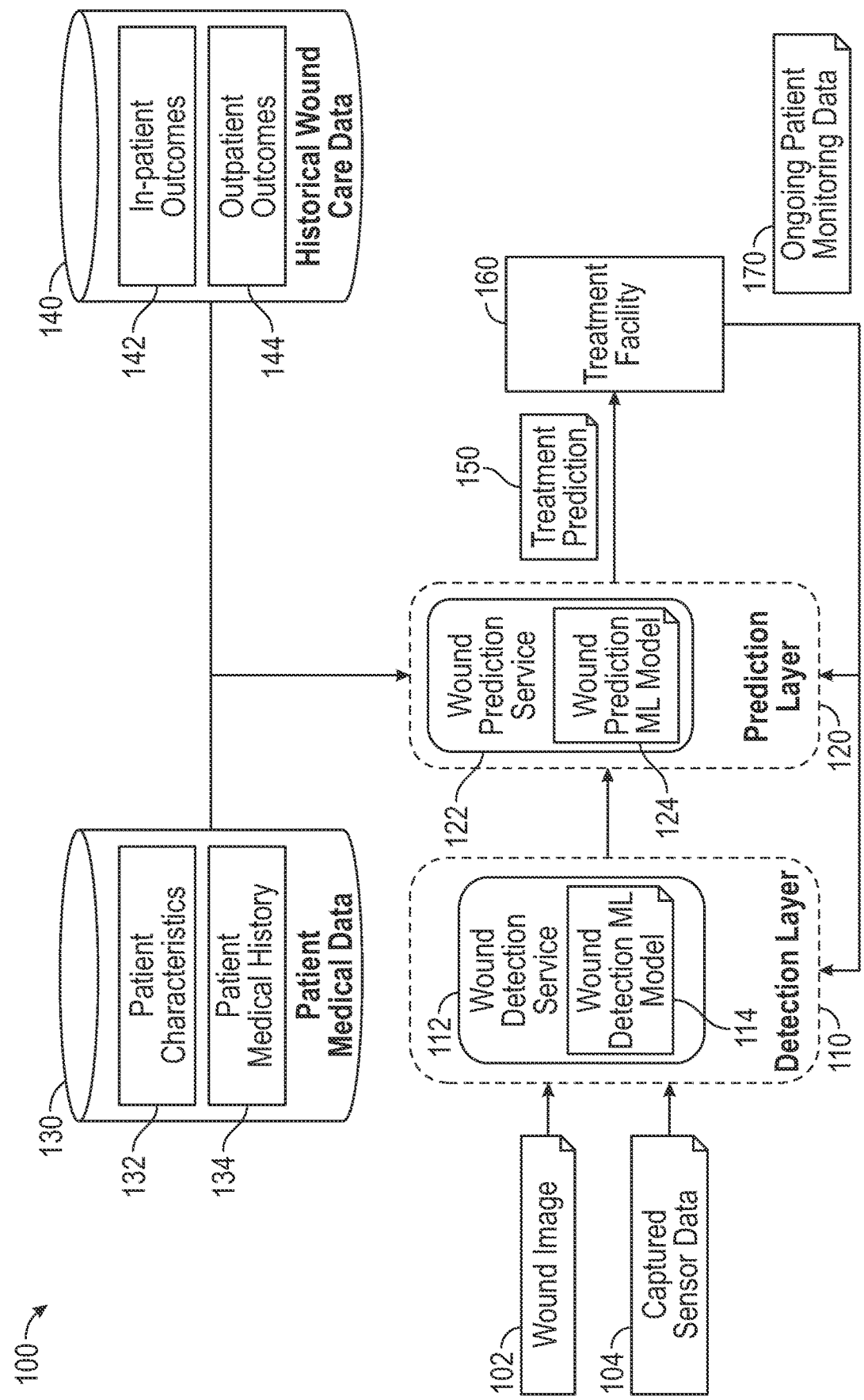
FIG. 1 depicts a computing environment for wound management and treatment using computer vision and ML, according to one embodiment.

Aspects of the present disclosure provide apparatuses, methods, processing systems, and non-transitory computer-readable mediums for improved wound management and treatment using computer vision and ML. As discussed above, a patient wound is typically treated using a care plan outlining various treatment tasks. This care plan, in existing practice, is commonly created manually by a care provider after examining the wound (e.g., in person). But this is inefficient, because it requires manual intervention, and it can be ineffective, because it is subject to human error and variance between care professionals. Alternatively, in existing practice, the care plan may be created using a pre-defined rubric or algorithm with pre-defined rules. This is also inefficient, because it requires a very large number of pre-defined rules and significant manual oversight, and ineffective because using the specific rubric or algorithm is extremely unlikely to be effective for all patients and all wounds. Accordingly, existing practices may generally lead to inconsistent and ineffective patient care outcomes.

In aspects described herein, a care plan for treating a patient wound can instead be created automatically using a trained ML model, based on a captured image of the wound or other captured sensor data. For example, a patient or care provider can capture an image of a patient wound. Computer vision techniques (e.g., a suitable ML model, as discussed further below) can be used to analyze the image and detect various characteristics of the wound from the image. A suitable prediction ML model (e.g., a deep learning neural network (DNN)) can be trained to predict a care plan for the patient wound, based on the detected wound characteristics and additional information about the patient. For example, the prediction ML model can use patient characteristics (e.g., demographic information, medication information, and assessment information) and patient medical history (e.g., prior medical conditions and treatments for the patient), along with the detected wound characteristics, to predict a care plan for the wound. This care plan can outline a set of treatment tasks to follow in treating the wound. Beneficially, this can provide both technical advantages and advantages in treating a patient. For example, as discussed further below, this can provide technical advantages over conventional techniques in the healthcare field by reducing computation burden and shifting computational burden from prediction time (when computational resources may be tied up and results are likely to be time sensitive) to an earlier training phase (when computational resources can be scheduled and are likely to be more freely available). Further, as also discussed further below, this provides treatment benefits to the patient by providing a more accurate and consistent care plan, allowing for prophylactic early treatment when high priority issues are identified, and allowing for rapid adjustment of a care plan based on real-time monitoring.

In an embodiment, the prediction ML model can be trained to predict a care plan using data about historical wound care incidents. For example, the prediction ML model can receive data about prior patient wounds, including characteristics of the relevant patient and wound, the care plan used, the facility used, and the resolution of the treatment. As noted above, this data can be used to train the ML model to predict a care plan for a newly identified wound, based on characteristics of the wound (e.g., detected from an image using computer vision techniques) and the patient.

Further, the patient can be continuously monitored during treatment of the wound (e.g., automatically using suitable sensors or manually by care providers), and the prediction ML model can update the predicted care plan based on the monitoring data. For example, additional images of the wound can be captured during treatment, computer vision techniques can be used to detect characteristics of the wound as it is treated, from the captured images, and the prediction ML model can predict a revised care plan for the wound using the updated characteristics. Further, the progress of the treatment of the wound can be used to continuously train the prediction ML model to improve future predictions.

Thus, aspects described herein provide significant advantages compared to conventional approaches for generating care plans. For example, predicting a care plan for treating a patient wound automatically using a trained ML model, based on a captured image of the wound or other captured sensor data, provides for an accurate care plan while minimizing the needed computational resources for the prediction and shifting the computational burden from prediction time (e.g., when near real-time response may be needed) to an earlier training time (e.g., when resources can be easily dedicated to the training). In an embodiment, generating a care plan using a specific rubric or algorithm with pre-defined rules can be computationally expensive, because a very large number of rules are needed and parsing and following the rules is computationally expensive. Further, this computationally expensive analysis is done at the time the care plan is generated, when a rapid response is likely to be needed (e.g., so that the patient can be treated quickly).

Predicting a care plan for treating a patient wound automatically using a trained ML model, by contrast, is significantly less computationally expensive at the time the care plan is generated. For example, the prediction ML model can be trained up-front during a training phase, when rapid response is not necessary and computational resources are readily available. The trained ML model can then be used to rapidly, and computationally relatively cheaply, predict a care plan for the patient. This provides a significant technical advantage over prior techniques by shifting the computational burden from the prediction time, when a rapid response is needed and computational resources may be engaged in other tasks, to a planned training time when a rapid response is not necessary and computational resources are available.

As another example, predicting a care plan for treating a patient wound automatically using a trained ML model, based on a captured image of the wound or other captured sensor data, provides for a more accurate and well-defined prediction. In an embodiment, a care plan for a wound can be manually created by a care provider. But this leaves the risk of human error and allows for significant variances among human practitioners, which can result in a lack of certainty in the accuracy of the care plan. Predicting the care plan using a trained ML model can both lessen the risk of human error, and provide more certainty in the level of accuracy of the care plan. Further, the predicted care plan can itself be reviewed and refined by a care provider. This provides a starting point for the care provider with a more certain level of accuracy, and reduces the burden on the care provider to generate the care plan themselves.

Example Computing Environment

FIG. 1 depicts a computing environment 100 for wound management and treatment using computer vision and ML, according to one embodiment. In an embodiment, a captured wound image 102 is provided to a detection layer 110. For example, a patient may have a wound (e.g., bedsores, sutures, abrasions, lesions, or any other visible wound) that is detectable using an image capture device. The patient, a healthcare, a caretaker, or any other person can capture an image of the wound using the image capture device (e.g., a digital camera). For example, a patient or healthcare professional can use a camera integrated into a smartphone or tablet computer to capture the wound image 102, and can use a suitable secure application to provide the image to the detection layer 110. This is merely one example, and any suitable image capture device can be used by any suitable person, or entity, to capture the wound image 102. For example, an automated sensor could be used to automatically trigger image capture of the wound image 102 (e.g., during a medical examination). Further, the image capture device can operate outside the visual spectrum (e.g., an infrared sensor, an x-ray sensor, or any other suitable sensor).

In an embodiment, the captured wound image 102 is provided to the detection layer 110 using a suitable communication network. For example, the wound image 102 can be captured using a camera in a computing device (e.g., a smartphone or tablet computer camera) and can be transferred to the detection layer using the computing device. The computing device can use any suitable communication network, including the Internet, a wide area network, a local area network, or a cellular network, and can use any suitable wired or wireless communication technique (e.g., WiFi or cellular communication). This is merely one example, and the wound image 102 can be captured by a camera and provided to a computing device using any suitable technique (e.g., using storage medium or through a wired or wireless transmission from the camera to the computing device).

The detection layer 110 includes a wound detection service 112, which includes a wound detection ML model 114. In an embodiment, the wound detection service 112 facilitates transformation of incoming patient data (e.g., wound image 102). For example, as discussed below with regard to FIG. 2, the wound detection service 112 can be computer software service implemented in a suitable controller (e.g., the prediction controller 200 illustrated in FIG. 2) or combination of controllers. In an embodiment the detection layer 110, and the wound detection service 112, can be implemented using any suitable combination of physical compute systems, cloud compute nodes and storage locations, or any other suitable implementation. For example, the detection layer 110 could be implemented using a server or cluster of servers. As another example, the detection layer 110 can be implemented using a combination of compute nodes and storage locations in a suitable cloud environment. For example, one or more of the components of the detection layer 110 can be implemented using a public cloud, a private cloud, a hybrid cloud, or any other suitable implementation.

As one example, the wound detection service 112 can facilitate computer vision analysis of the wound image 102. In this example, the wound detection ML model 114 can be a suitable computer vision ML model (e.g., a DNN, support vector machine (SVM), or any other suitable ML model). In an embodiment, the wound detection ML model 114 can be trained to receive the wound image 102, and to recognize or detect various characteristics of the wound depicted in the image. These can include exterior characteristics (e.g., size and color), interior characteristics (e.g., size, color, and depth), location, and any other suitable characteristics. This is discussed further below with regard to FIGS. 4-5 and 8.

In an embodiment, the wound image 102 is merely one example of patient data that can be analyzed using the detection layer 110 (e.g., using the wound detection service 112 and the wound detection ML model 114). For example, captured sensor data 104 can also be provided to the detection layer 110. In an embodiment, the captured sensor data 104 includes data captured by sensors used during treatment or rehabilitation of a patient (e.g., captured during treatment of a wound). For example, the captured sensor data 104 can include data from negative pressure wound therapy devices, oxygen and intubation devices, monitored pressure and drainage devices, or any other suitable devices.

In an embodiment, the wound detection service 112 can further facilitate analysis of the captured sensor data 104. For example, the wound detection service 112 can use a wound detection ML model 114 to detect and identify characteristics of the patient's wound based on the captured sensor data. In an embodiment, the wound detection ML model 114 can be any suitable ML model (e.g., a DNN, a decision tree, a random forest, a support vector machine, and other ML model types) trained to detect and identify characteristics of the patient's wound.

Further, in an embodiment, the wound detection ML model 114 can include multiple ML models trained to detect wound characteristics from different data. For example, one ML model could be trained to use computer vision techniques to identify wound characteristics from the wound image 102, another ML model could be trained to detect wound characteristics based on sensor data from a wound therapy device, and another ML model could be trained to detect wound characteristics based on sensor data from monitored pressure devices. In some aspects, these different models may be ensemble to produce a prediction. This is merely an example, and the wound detection ML model could instead be trained to use data from multiple sources (e.g., the wound image 102 and captured sensor data 104), together, to detect and identify characteristics of the patient's wound.

In an embodiment, the detection layer 110 provides wound detection data to a prediction layer 120. For example, the wound detection service 112 can use the wound detection ML model 114 to detect characteristics of a patient wound, using the wound image 102, the captured sensor data 104, or both. The detection layer 110 can provide these wound characteristics to the prediction layer 120.

The prediction layer 120 includes a wound prediction service 122 and a wound prediction ML model 124. In an embodiment, the wound prediction service 122 facilitates prediction of treatment and rehabilitation information for the patient wound. For example, the wound prediction service 122 can use the wound prediction ML model 124 to determine a treatment prediction 150 (e.g., a wound care plan) and predict any other suitable treatment and rehabilitation information for the patient wound. This is discussed further below with regard to FIG. 7.

As discussed below with regard to FIG. 2, the wound prediction service 122 can be computer software service implemented in a suitable controller (e.g., the prediction controller 200 illustrated in FIG. 2) or combination of controllers. In an embodiment the prediction layer 120, and the wound prediction service 122, can be implemented using any suitable combination of physical compute systems, cloud compute nodes and storage locations, or any other suitable implementation. For example, the prediction layer 120 could be implemented using a server or cluster of servers. As another example, the prediction layer 120 can be implemented using a combination of compute nodes and storage locations in a suitable cloud environment. For example, one or more of the components of the prediction layer 120 can be implemented using a public cloud, a private cloud, a hybrid cloud, or any other suitable implementation.

As discussed above, the prediction layer 120 uses the detected characteristics of the patient wound (e.g., the output from the detection layer 110) to predict the treatment and rehabilitation information for the patient wound. In an embodiment, however, the wound characteristics detected by the detection layer 110 are not sufficient to allow the prediction layer 120 to accurately predict the treatment and rehabilitation information for the patient wound. For example, merely identifying the characteristics of the wound may not be sufficient to identify a suitable treatment plan for the patient, and may not be sufficient to identify a suitable treatment facility for the patient.

In an embodiment, the prediction layer 120 can further receive, and use, patient medical data 130 and historical wound care data 140. For example, the patient medical data 130 can include patient characteristics 132 and patient medical history 134. In an embodiment, the patient characteristics 132 can include patient demographics (e.g., age, height, weight), patient medications (e.g., a listing of medications for the patient), patient assessment data (e.g., intake assessment data, discharge assessment data, activities of daily living (ADL) assessment data), or any other suitable patient characteristics. This is discussed further below with regard to FIG. 9. In an embodiment, the patient medical history 134 can include medical condition data (e.g., diagnosis, onset, treatment, and resolution) for any prior medical conditions. This is discussed further below with regard to FIG. 10.

In an embodiment, the historical wound care data 140 can include data about in-patient outcomes 142 and outpatient outcomes 144, for various patients and various wounds. For example, the historical wound care data 140 can include wound characteristics for a wound (e.g., exterior characteristics, interior characteristics, and location), patient characteristics for the patient with the wound (e.g., demographics, medications, assessments, and medical history), care plan history for the wound (e.g., treatments used), facility characteristics for treatment of the wound (e.g., type of facility, staffing at the facility, and available resources at the facility), resolution data (e.g., time and resources used in treatment, and result of the treatment), and any other suitable historical wound care data. In an embodiment, the patient medical data 130 provides data about the particular patient with the wound, while the historical wound care data 140 provides data about historical treatments and resolutions for a variety of wounds and patients. Further, in an embodiment, the historical wound care data 140 has had any personally identifying patient information removed.

In an embodiment, the patient medical data 130 and the historical wound care data 140 are provided to the prediction layer 120 using a suitable communication network. For example, the patient medical data 130 and the historical wound care data 140 can be stored in one or more suitable electronic databases (e.g., a relational database, a graph database, or any other suitable database) or other electronic repositories (e.g., a cloud storage location, an on-premises network storage location, or any other suitable electronic repository). The patient medical data 130 and the historical wound care data 140 can be provided from the respective electronic repositories to the prediction layer 120 using any suitable communication network, including the Internet, a wide area network, a local area network, or a cellular network, and can use any suitable wired or wireless communication technique (e.g., WiFi or cellular communication).

As discussed above, in an embodiment, the wound prediction service 122 uses the wound prediction ML model 124 to predict treatment and rehabilitation information for the patient wound. For example, the wound prediction ML model 124 can be a suitable supervised ML model (e.g., a DNN) trained to generate a treatment prediction 150 for the patient wound from a combination of wound characteristics for the particular wound at issue (e.g., output from the detection layer 110), patient medical data 130, and historical wound care data 140. This is discussed further below with regard to FIG. 3. For example, the wound prediction ML model 124 can be selected based on initial analysis of the input data (e.g., the wound characteristics, patient medical data 130, and historical wound care data 140). In an embodiment, a basic technique can be initially selected (e.g., logistic regression), data can be converted to a numerical format, and based on initial analysis data transformation and ML techniques can be chosen. This is merely an example, and any suitable supervised, or unsupervised, techniques can be used.

For example, the wound prediction ML model can predict a care plan for the wound, including recommended treatments and medications. This is one example of a treatment prediction 150. In an embodiment, the care plan (or any other suitable treatment prediction 150) can be provided to a treatment facility 160. In an embodiment, the treatment facility 160 can be any suitable in-patient or out-patient treatment facility. Further, in an embodiment, the care plan can be provided directly to the patient or to the patient's medical care provider. This is discussed further below with regard to FIG. 13. In an embodiment, the treatment prediction 150 is provided to any, or all of the treatment facility, the patient, and the care provider using a suitable communication network. For example, the treatment prediction 150 can be provided from the prediction layer 120 to the destination (e.g., treatment facility, patient, or care provider) using any suitable communication network, including the Internet, a wide area network, a local area network, or a cellular network, and can use any suitable wired or wireless communication technique (e.g., WiFi or cellular communication).

In an embodiment, the treatment prediction 150 is used to treat the patient. For example, the treatment prediction 150 can be a wound care plan provided to the treatment facility 160. Care providers at the treatment facility 160, or the patient them self, can use the wound care plan to treat the wound (e.g., using the identified treatments and medications). In an embodiment, the treatment of the wound can be monitored, and ongoing patient monitoring data 170 can be gathered. For example, repeated images of the wound can be captured, other sensor data can be provided, care providers can provide assessment data, and any other suitable data can be gathered. Further, in an embodiment, captured data can be maintained in suitable repository (e.g., an electronic database) and used for training (e.g., training the wound prediction ML model 124). This data, and all training data, can be stripped of any personally identifying patient information.

In an embodiment, this ongoing patient monitoring data 170 can be provided to the detection layer 110, the prediction layer 120, or both, and used to refine the treatment prediction 150. For example, captured images or other captured sensor data can be provided to the detection layer 110 and analyzed in the same way as the wound image 102 and the captured sensor data 104 (e.g., to identify ongoing wound characteristics as the wound is treated). As another example, updated patient medical data can be provided to the prediction layer 120 and analyzed in the same way as the patient medical data 130.

Further, in an embodiment, the ongoing patient monitoring data 170 can be used to continuously train the wound prediction ML model 124. For example, the wound prediction ML model 124 can determine, from the ongoing patient monitoring data 170 (e.g., from detected wound characteristics of additional captured images of the wound as it is treated), whether the wound is progressing in treatment and how quickly it is progressing. As one example, the color, shape, size, condition (e.g., oozing or dry), or depth of the wound may change during treatment, indicating progress in healing. The wound prediction service 122 can use the prior predicted care plan, and the result of the care as indicated by the ongoing patient monitoring data, as additional training data to further train the wound prediction ML model 124 to predict a care plan that provides successful treatment to patients.

Figure 2:
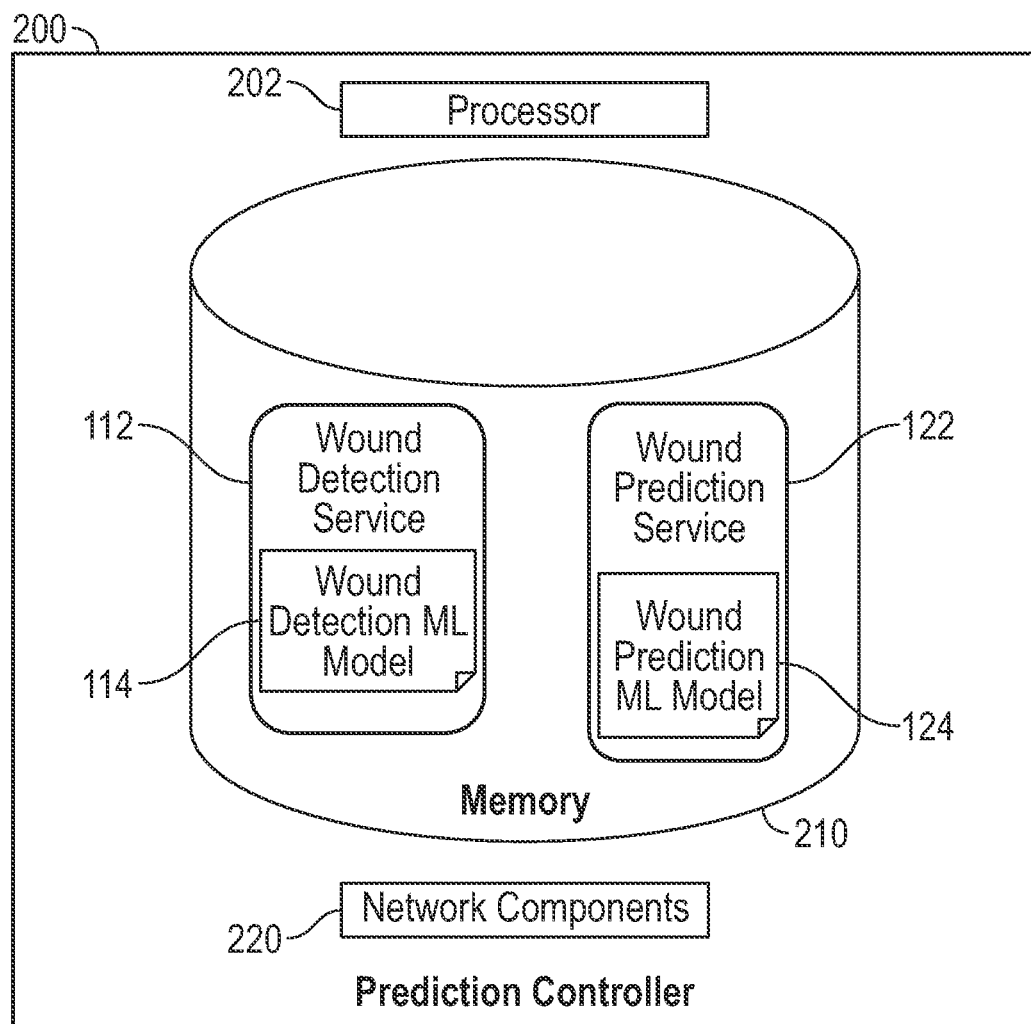
FIG. 2 depicts a block diagram for a prediction controller for wound management and treatment using computer vision and ML, according to one embodiment.

FIG. 2 depicts a block diagram for a prediction controller 200 for wound management and treatment using computer vision and ML, according to one embodiment. The controller 200 includes a processor 202, a memory 210, and network components 220. The memory 210 may take the form of any non-transitory computer-readable medium. The processor 202 generally retrieves and executes programming instructions stored in the memory 210. The processor 202 is representative of a single central processing unit (CPU), multiple CPUs, a single CPU having multiple processing cores, graphics processing units (GPUs) having multiple execution paths, and the like.

The network components 220 include the components necessary for the controller 200 to interface with a suitable communication network (e.g., a communication network interconnecting various components of the computing environment 100 illustrated in FIG. 1, or interconnecting the computing environment 100 with other computing systems). For example, the network components 220 can include wired, WiFi, or cellular network interface components and associated software. Although the memory 210 is shown as a single entity, the memory 210 may include one or more memory devices having blocks of memory associated with physical addresses, such as random access memory (RAM), read only memory (ROM), flash memory, or other types of volatile and/or non-volatile memory.

The memory 210 generally includes program code for performing various functions related to use of the prediction controller 200. The program code is generally described as various functional "applications" or "modules" within the memory 210, although alternate implementations may have different functions and/or combinations of functions. Within the memory 210, the wound detection service 112 facilitates detecting wound characteristics from captured sensor data (e.g., captured images and other captured sensor data), using the wound detection ML model 114. This is discussed further below with regard to FIGS. 4-6. The wound prediction service 122 facilitates predicting treatment and rehabilitation information for a wound, using the wound prediction ML model 124. This is discussed further below with regard to FIGS. 3 and 7.

While the controller 200 is illustrated as a single entity, in an embodiment, the various components can be implemented using any suitable combination of physical compute systems, cloud compute nodes and storage locations, or any other suitable implementation. For example, the controller 200 could be implemented using a server or cluster of servers. As another example, the controller 200 can be implemented using a combination of compute nodes and storage locations in a suitable cloud environment. For example, one or more of the components of the controller 200 can be implemented using a public cloud, a private cloud, a hybrid cloud, or any other suitable implementation.

Although FIG. 2 depicts the wound detection service 112, the wound prediction service 122, the wound detection ML model 114, and the wound prediction ML model 124, as being mutually co-located in memory 210, that representation is also merely provided as an illustration for clarity. More generally, the controller 200 may include one or more computing platforms, such as computer servers for example, which may be co-located, or may form an interactively linked but distributed system, such as a cloud-based system, for instance. As a result, processor 202 and memory 210 may correspond to distributed processor and memory resources within the computing environment 100. Thus, it is to be understood that any, or all, of the wound detection service 112, the wound prediction service 122, the wound detection ML model 114, and the wound prediction ML model 124 may be stored remotely from one another within the distributed memory resources of the computing environment 100.

Figure 3:
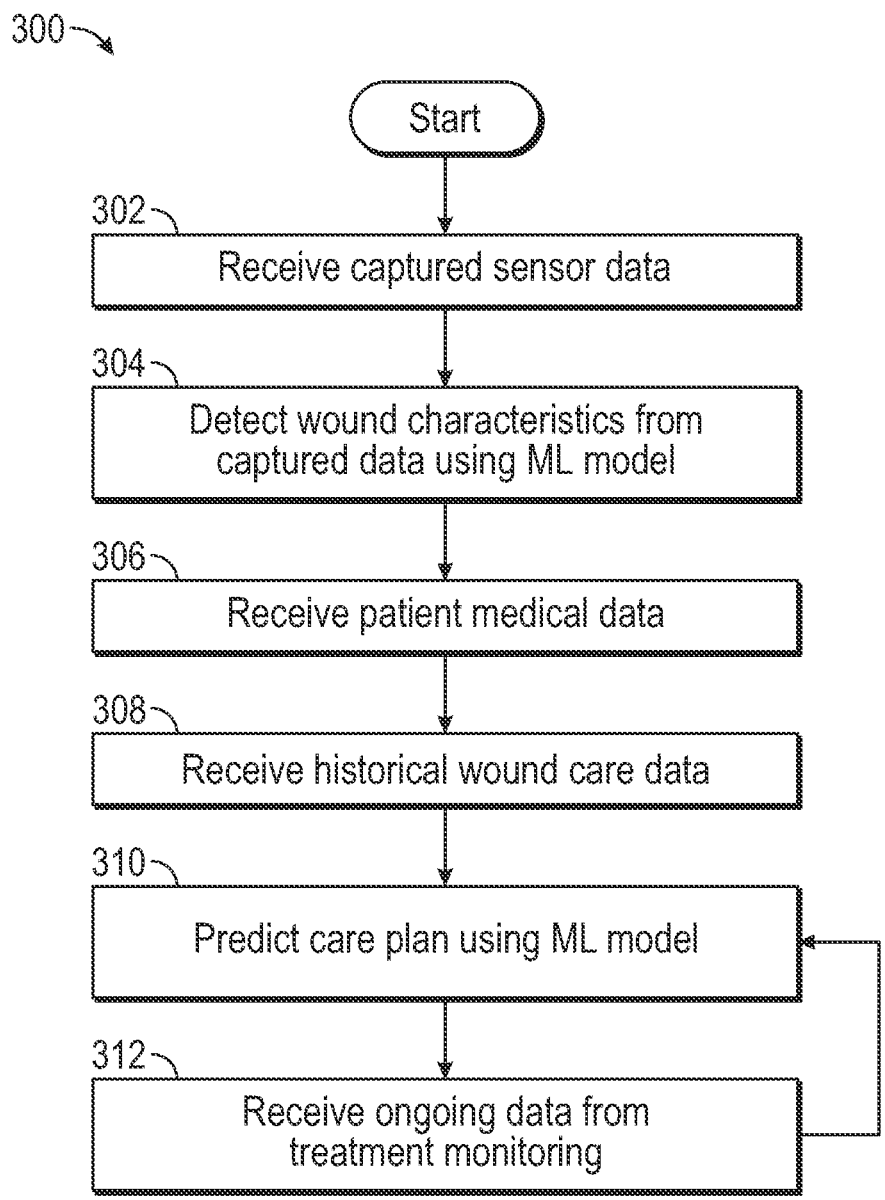
FIG. 3 is a flowchart illustrating wound management and treatment using computer vision and ML, according to one embodiment.

FIG. 3 is a flowchart 300 illustrating wound management and treatment using computer vision and ML, according to one embodiment. At block 302 a wound detection service (e.g., the wound detection service 112 illustrated in FIGS. 1-2) receives captured sensor data relating to a patient wound. For example, as discussed above in relation to FIG. 1, in an embodiment the wound detection service can receive a captured wound image (e.g., the wound image 102 illustrated in FIG. 1), captured sensor data (e.g., the captured sensor data 104 illustrated in FIG. 1), or both.

At block 304, the wound detection service detects wound characteristics from the captured data using an ML model. For example, the wound detection service can use a captured image, sensor data, or both to detect exterior characteristics (e.g., size and color), interior characteristics (e.g., size, color, and depth), location, and any other suitable characteristics of the wound. As discussed above in relation to the wound detection ML model 114 illustrated in FIG. 1, the wound detection service can use any suitable ML model, or combination of ML models, to detect wound characteristics from the captured sensor data. This is discussed further below with regard to FIGS. 4-6.

At block 306, a prediction service (e.g., the wound prediction service 122 illustrated in FIGS. 1-2) receives patient medical data. For example, the prediction service can receive the patient medical data 130 illustrated in FIG. 1. This can include patient characteristics (e.g., patient demographics, patient medications, patient assessment data, or any other suitable patient characteristics) and patient medical history (e.g., medical condition data for any prior medical conditions). This is discussed further below with regard to FIGS. 9-10.

At block 308, the prediction service receives historical wound care data. For example, the prediction service can receive the historical wound care data 140 illustrated in FIG. 1. This can include historical data about in-patient outcomes and outpatient outcomes, for various patients and various wounds. This is discussed further below with regard to FIG. 11. In an embodiment, the prediction service uses the historical wound care data for ongoing training of the prediction ML model. Alternatively, the prediction service does not receive the historical wound care data. In this example, the historical wound care data is used to train the prediction ML model (e.g., as discussed below in relation to FIG. 12) but is not used for inference (e.g., for prediction).

At block 310, the prediction service predicts a care plan for the patient wound using an ML model. For example, the prediction service can use the wound prediction ML model 124 illustrated in FIGS. 1-2 to predict the care plan. The prediction ML model can be any suitable ML model trained to use the wound characteristics (e.g., detected from captured sensor data using an ML model at block 304), the patient medical data received at block 306, and the historical wound care data received at block 308, to predict a care plan for the patient wound. This can include predicting treatments, medications, and any other suitable care for the patient wound. This is discussed further below with regard to FIG. 7.

As illustrated the prediction ML model uses all of the wound characteristics, the patient medical data, and the historical wound care data, to predict the care plan. But this is merely an example. Alternatively, or in addition, the prediction ML model can use any subset of this data (e.g., where some of this data is unavailable for a given patient wound). For example, the prediction ML model can use the wound characteristics and patient medical data, without historical wound care data, or wound characteristics and historical wound care data, without patient medical data. In an embodiment this may result in a slight loss of accuracy in predicting the care plan, but the predicted care plan is still significantly improved over prior techniques (e.g., manual creation of the care plan).

In an embodiment, the prediction service can further identify a prophylactic treatment task for the wound (e.g., a treatment task intended to quickly prevent further disease or issues with the wound). For example, the prediction service can use the wound characteristics, the patient medical data, including but not limited to specific health related data associated with one or more patients, such as age, weight, medical conditions, demographics, or other such data, or both to identify a high priority treatment task (e.g. a medication, bandaging, or another medical procedure) needed for the wound (e.g., bedsores, sutures, abrasions, lesions, or any other wound). As one example, a wound could be identified as requiring immediate medical treatment (e.g., bandaging, a surgical procedure, a particular medication, or any other suitable treatment), to prevent further disease or issues with the wound. Thus, for example, a bedsore, suture, abrasion, or lesion could be identified as requiring immediate medication, immediate bandaging, or another immediate medical procedure. The prediction service can transmit an alert (e.g., an e-mail, SMS message, telephone call, or another form of electronic message) describing the treatment task to a care provider for the patient (e.g., via a care facility for the patient) or to the patient themselves. The care provider or patient can then treat the wound using the treatment task. In an embodiment, the prediction service can identify this treatment task prior to completing the prediction of the care plan. For example, the prediction service can identify a high priority treatment task while predicting the care plan, and can transmit the alert prior to completing the prediction of the care plan. In an embodiment this allows for a rapid alert for the treatment task, without waiting for complete prediction of the care plan.

At block 312, the prediction service receives ongoing data form treatment monitoring. For example, the prediction service can receive additional sensor data (e.g., additional images) captured during treatment and rehabilitation of the patient wound. This data can be captured at a treatment facility (e.g., an in-patient or out-patient facility), by a suitable medical professional or by the patient them self. In an embodiment, the prediction service can use the ongoing data to further refine the wound care plan.

Example of Detecting Wound Characteristics from a Captured Image

Figure 4:
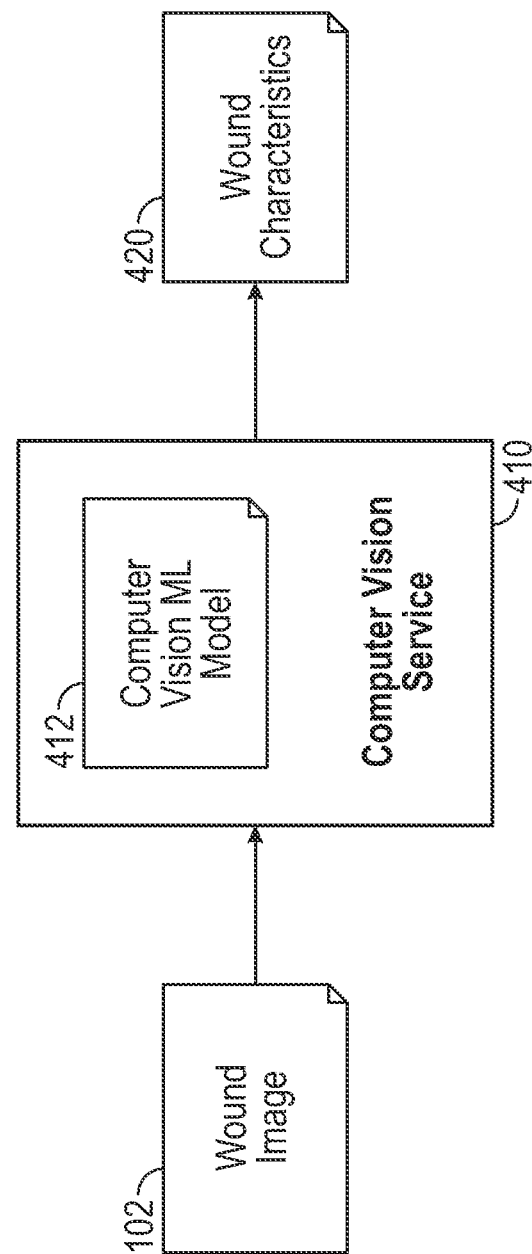
FIG. 4 illustrates detecting wound characteristics from a captured image using computer vision, according to one embodiment.

FIG. 4 illustrates detecting wound characteristics from a captured image using computer vision, according to one embodiment. In an embodiment, FIG. 4 provides one example of detecting wound characteristics from captured data using an ML model, discussed above in relation to block 304 illustrated in FIG. 3. A wound image 102 (e.g., as discussed above in relation to FIG. 1) is provided to a computer vision service 410 and a computer vision ML model 412. In an embodiment, the wound image 102 is an image of the patient wound captured using any suitable image capture device (e.g., a camera, a medical imaging device, or any other suitable image capture device).

In an embodiment, the computer vision service 410 is one example of a wound detection service 112, and the computer vision ML model 412 is one example of a wound detection ML model 114, both illustrated in FIGS. 1-2. As discussed above, in an embodiment the wound detection service 112 can detect wound characteristics from a variety of captured sensor data, including a captured image or captured sensor data from treatment devices, using the wound detection ML model. The computer vision service 410 detects wound characteristics 420 from the wound image 102 using the computer vision ML model 412.

In an embodiment, the computer vision ML model 412 can be any suitable ML model. For example, a non-neural network ML model can be used (e.g., a SVM). This can use any suitable object detection, recognition, or identification technique. As another example, a neural network ML model can be used (e.g., a CNN), and can use any suitable object detection, recognition, or identification technique.

As discussed above, the wound characteristics 420 can include any suitable wound characteristics. These can include exterior characteristics (e.g., size and color), interior characteristics (e.g., size, color, and depth), location, and any other suitable characteristics. This is discussed further below with regard to FIG. 8.

Figure 5:
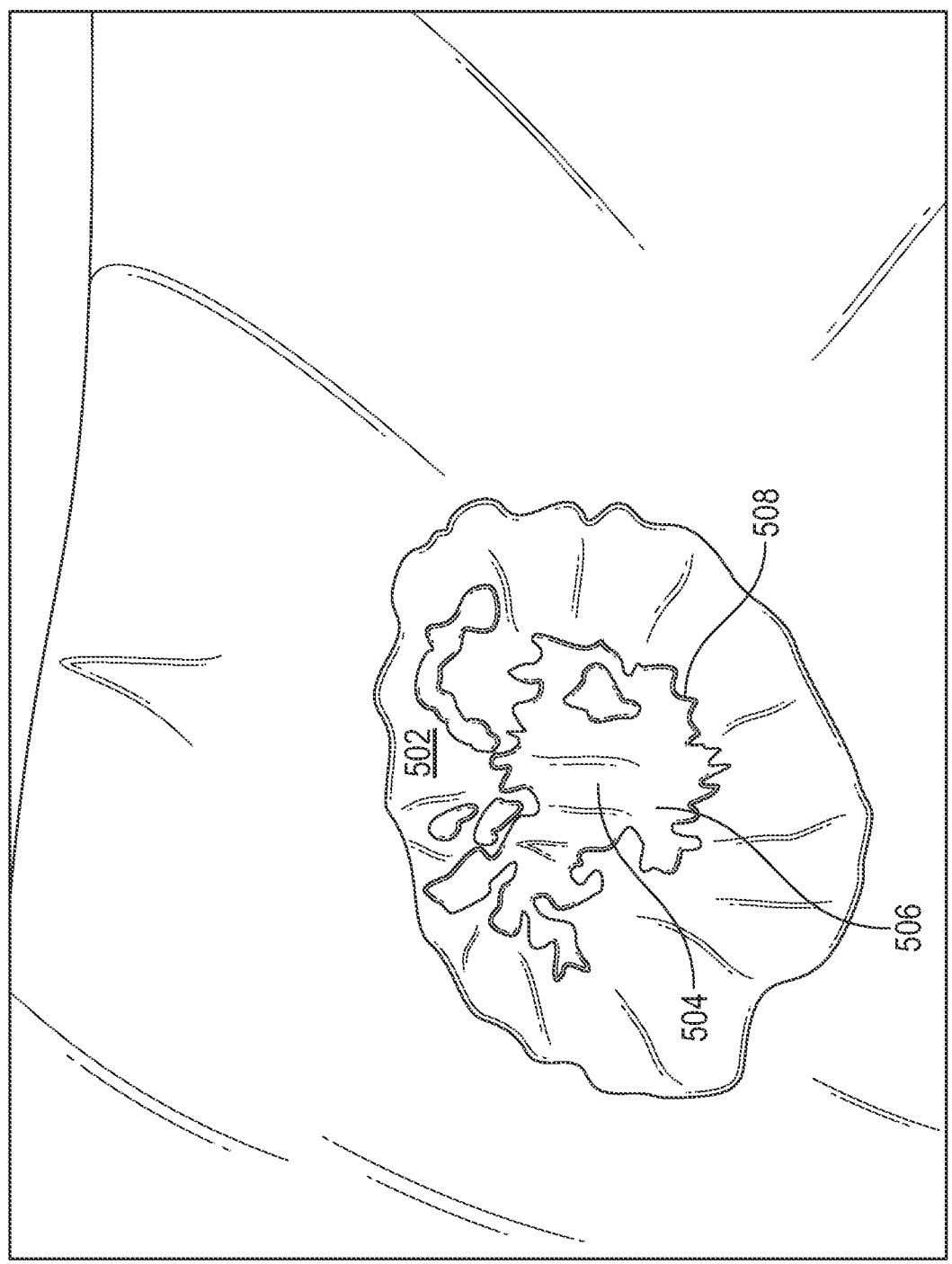
FIG. 5 depicts an example of detecting wound characteristics from a captured image using computer vision, according to one embodiment.

FIG. 5 depicts an example of detecting wound characteristics from a captured image using computer vision, according to one embodiment. In an embodiment, a captured image depicts a wound on a patient. As discussed above, a suitable wound detection service (e.g., the computer vision service 410 illustrated in FIG. 4) detects characteristics of the wound from the image, using a suitable wound detection ML model (e.g., the computer vision ML model 412 illustrated in FIG. 4). For example, the wound detection service can detect an exterior size 502 and an exterior color 508. As another example, the wound detection service can detect an interior size and color 506, and a depth 504

Example of Training a Computer Vision ML Model

Figure 6:
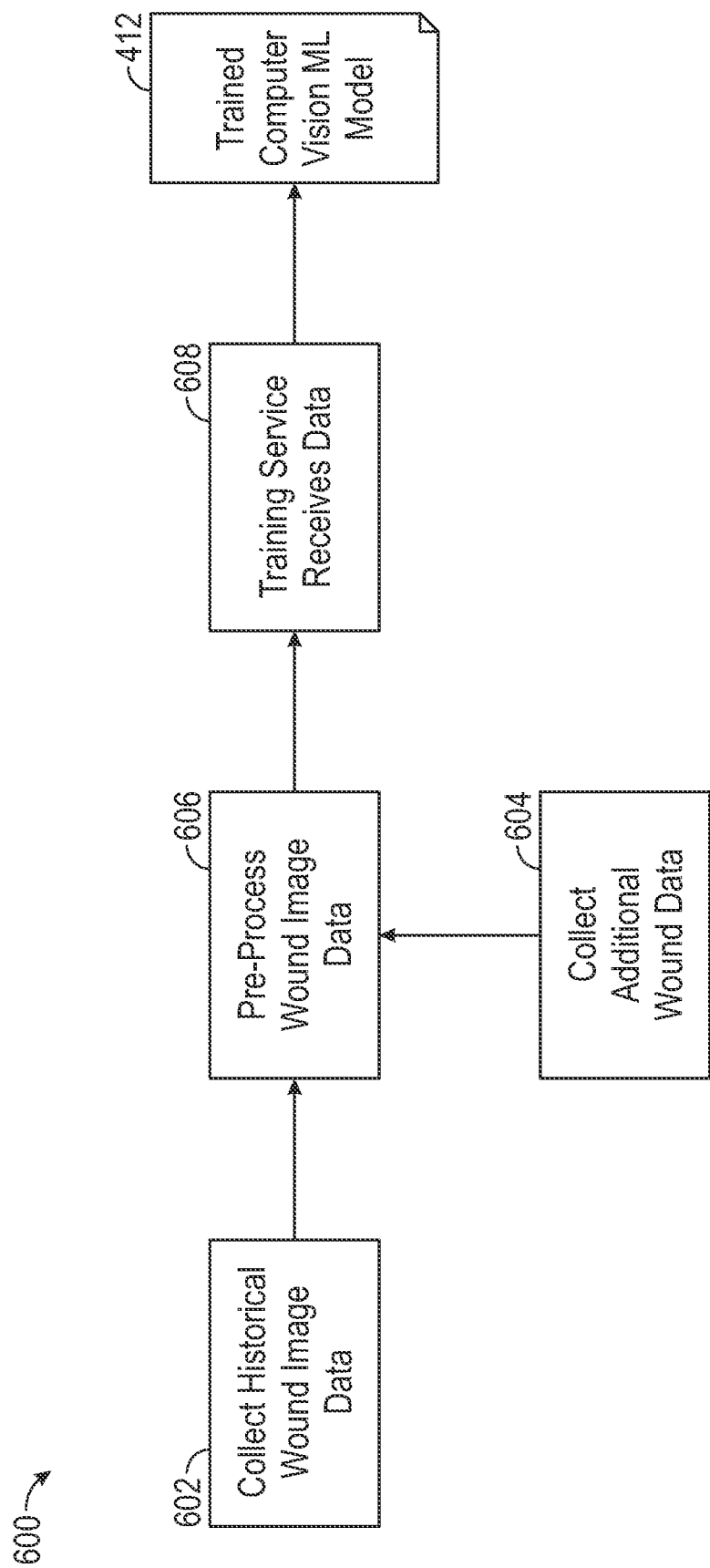
FIG. 6 is a flowchart illustrating training a computer vision ML model for wound management and treatment, according to one embodiment.

FIG. 6 is a flowchart 600 illustrating training a computer vision ML model for wound management and treatment, according to one embodiment. This is merely an example, and in an embodiment a suitable unsupervised technique could be used (e.g., without requiring training). At block 602, a training service (e.g., a human administrator or a software or hardware service) collects historical wound image data. For example, a wound detection service (e.g., the wound detection service 112 illustrated in FIGS. 1 and 2) can be configured to act as the training service and collect previously captured images of patient wounds (e.g., gathered over time). This is merely an example, and any suitable software or hardware service can be used (e.g., a wound detection training service).

At block 606, the training service (or other suitable service) pre-processes the collected historical wound image data. For example, the training service can create feature vectors reflecting the values of various features, for each collected wound image. At block 608, the training service receives the feature vectors and uses them to train a trained computer vision ML model 412 (e.g., the computer vision model 412 illustrated in FIG. 4).

In an embodiment, at block 604 the training service also collects additional wound data (e.g., data generated from in-person evaluation of the wound). At block 606, the training service can also pre-process this additional wound data. For example, the feature vectors corresponding to the historical wound image data can be further annotated using the additional wound data. Alternatively, or in addition, additional feature vectors corresponding to the additional wound data can be created. At block 608, the training service uses the pre-processed additional wound data during training to generate the trained computer vision ML model 412.

In an embodiment, the pre-processing and training can be done as batch training. In this embodiment, all data is pre-processed at once (e.g., all historical wound image data and additional wound data), and provided to the training service at block 608. Alternatively, the pre-processing and training can be done in a streaming manner. In this embodiment, the data is streaming, and is continuously pre-processed and provided to the training service. For example, it can be desirable to take a streaming approach for scalability. The set of training data may be very large, so it may be desirable to pre-process the data, and provide it to the training service, in a streaming manner (e.g., to avoid computation and storage limitations). Further, in an embodiment, a federated learning approach could be used in which multiple healthcare entities contribute to training a shared model.

Example of Predicting a Wound Care Plan

Figure 7:
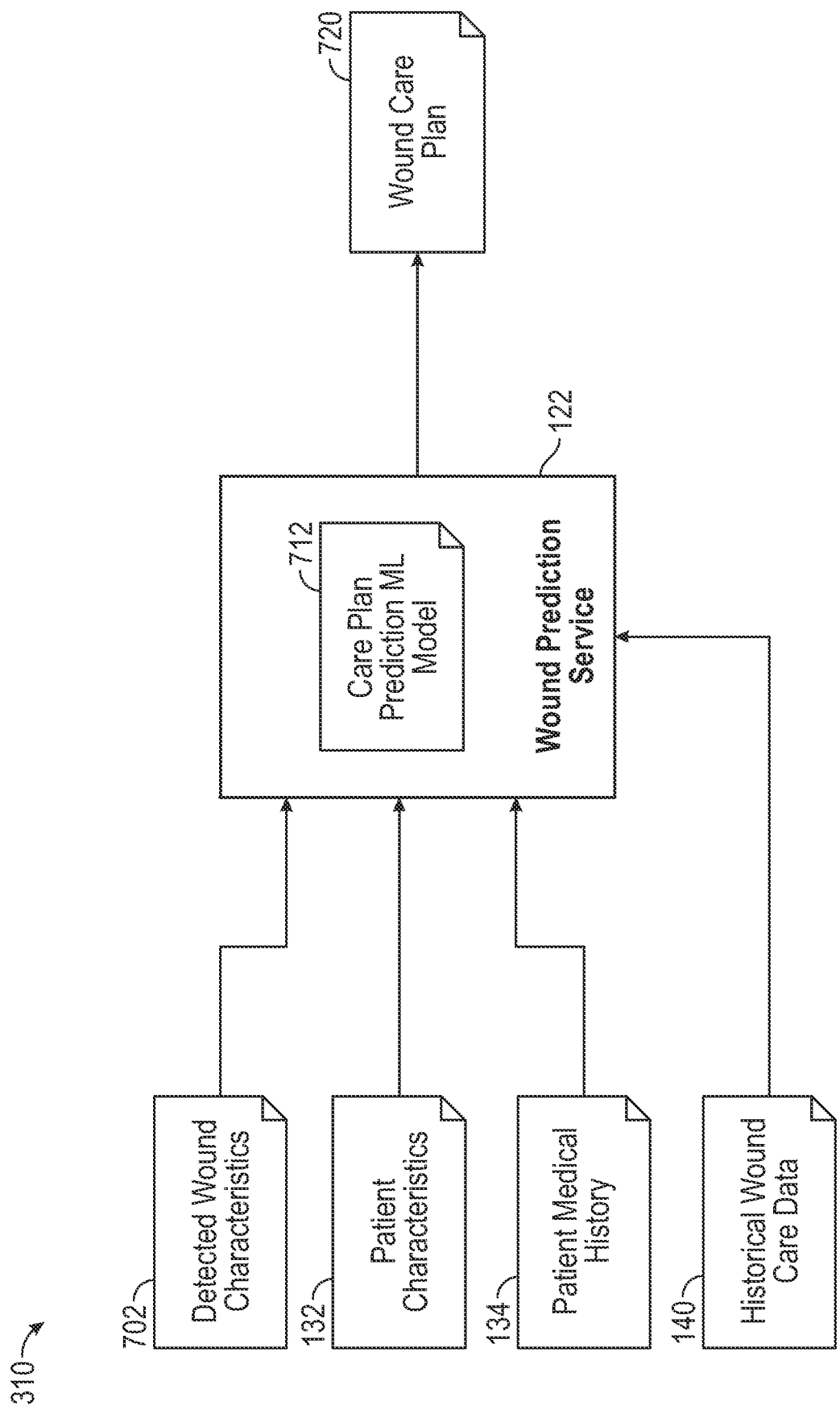
FIG. 7 depicts predicting a wound care plan using an ML model, according to one embodiment.

FIG. 7 depicts predicting a wound care plan using an ML model, according to one embodiment. In an embodiment, FIG. 7 corresponds with block 310 illustrated in FIG. 3, above. A wound prediction service 122, as discussed above in relation to FIGS. 1-2, is associated with a care plan prediction ML model 712. In an embodiment, the care plan prediction ML model 712 is one example of a wound prediction ML model (e.g., one example of the wound prediction ML model 124 illustrated in FIGS. 1-2). For example, as illustrated the wound prediction service 122 uses the care plan prediction ML model 712 to predict a wound care plan 720.

In an embodiment, the wound prediction service 122 uses multiple types of data to predict the wound care plan 720, using the care plan prediction ML model 712. For example, the wound prediction service 122 can use detected wound characteristics 702. In an embodiment, the detected wound characteristics 702 are generated by a wound detection service (e.g., the wound detection service 112 illustrated in FIGS. 1-2) using a wound detection ML model (e.g., the wound detection ML model 114 illustrated in FIGS. 1-2) by detecting wound characteristics from captured data (e.g., a wound image 102, captured sensor data 104, or both). For example, as illustrated in FIG. 4, a computer vision service 410 can use a computer vision ML model 412 to detect wound characteristics 420 from a wound image 102. As discussed below in relation to FIG. 8, in an embodiment the detected wound characteristics 702 can include exterior characteristics (e.g., size, color), interior characteristics (e.g., size, color, depth), location, and any other suitable characteristics.

In addition, the wound prediction service 122 can use patient characteristics 132 (e.g., as discussed above in relation to FIG. 1) to predict the wound care plan 720, using the care plan prediction ML model 712. As discussed below in relation to FIG. 9, the patient characteristics 132 can include patient demographics (e.g., age, height, weight), patient medications (e.g., a listing of medications for the patient), patient assessment data (e.g., intake assessment data, discharge assessment data, activities of daily living (ADL) assessment data), or any other suitable patient characteristics.

Further, the wound prediction service 122 can use a patient medical history 134 (e.g., as discussed above in relation to FIG. 1) to predict the wound care plan 720, using the care plan prediction ML model 712. As discussed below in relation to FIG. 10, the patient medical history 134 can include medical condition data (e.g., diagnosis, onset, treatment, and resolution) for any prior medical conditions.

The wound prediction service 122 can further use historical wound care data 140 (e.g., as discussed above in relation to FIG. 1) to predict the wound care plan 720, using the care plan prediction ML model 712. As discussed below in relation to FIG. 11, the historical wound care data 140 can include wound characteristics for a wound (e.g., exterior characteristics, interior characteristics, and location), patient characteristics for the patient with the wound (e.g., demographics, medications, assessments, and medical history), care plan history for the wound (e.g., treatments used), facility characteristics for treatment of the wound (e.g., type of facility, staffing at the facility, and available resources at the facility), resolution data (e.g., time and resources used in treatment, and result of the treatment), and any other suitable historical wound care data. As discussed above in relation to FIG. 1, in an embodiment the patient characteristics 132 and patient medical history 134 provide data about the particular patient with the wound, while the historical wound care data 140 provides data about historical treatments and resolutions for a variety of wounds and patients.

In an embodiment, the wound prediction service 122 uses the historical wound care data 140 for ongoing training of the care prediction ML model 712. For example, because training the care prediction ML model 712 may be computationally expensive, the wound prediction service can train the care prediction ML model 712 at suitable intervals (e.g., hourly, daily, weekly) or based on triggering events (e.g., after a threshold number of new observations are received, upon request from an administrator, or at any other suitable interval). Alternatively, the wound prediction service 122 does not receive the historical wound care data 140. In this example, the historical wound care data 140 is used to train the prediction ML model (e.g., as discussed below in relation to FIG. 12) but is not used for inference (e.g., for prediction of the wound care plan 720).

In an embodiment, the wound care plan 720 provides a treatment plan for treating the patient wound. For example, the wound care plan 720 can include a set of tasks (e.g., medication tasks, treatment tasks, rehabilitation tasks, physical training tasks, or any other suitable tasks) for the patient, the patient's healthcare provider, the patient's caretaker, or other assisting personnel, to perform. The wound care plan 720 can be predicted by the care plan prediction ML model 712 so that adhering to the wound care plan 720 will provide optimal, or preferred, treatment to the patient. As discussed above, a care plan is typically generated manually (e.g., by a healthcare provider) or programmatically using a specific rubric or algorithm. This can be inefficient (e.g., because it requires manual intervention) and ineffective. In an embodiment, the wound care plan 720 generated using the care plan prediction ML model 712 provides both effective and efficient treatment. Further, in an embodiment, a healthcare provider can review the generated wound care plan 720 and provide any suitable revisions. This can still greatly improve efficiency and effectiveness in creating the care plan, by assisting the healthcare provider.

In an embodiment, the wound care plan 720 can include treatment tasks relating to actions to be taken by the patient. For example, the wound care plan 720 can include information related to preferred nutrition for the patient. In this example, the patient's compliance with the preferred nutrition can further be identified during treatment (e.g., using sensors available at the location where the patient is being treated). As another example, the wound care plan 720 can include information about a preferred humidity level to treat the patient's wound. The humidity level at the patient's living facility can be monitored (e.g., using suitable sensors) and the patient can be encouraged, or assisted, in maintaining a preferred humidity level for treatment of the wound.

As another example, the wound care plan 720 can include sleep treatment tasks. For example, the wound care plan 720 can outline amounts of sleep and sleep positions. In this example, a patient with a wound on a particular location on their body (e.g., a pressure sore) could be treated by describing a sleep position, duration, or both for the patient to assist in treating the wound (e.g., a position or duration relieving the pressure on the wound). The patient's sleep could be monitored and the patient could be assisted with complying with the sleep treatment task. For example, one or more sensors (e.g., including smart wearable devices, smart sleep devices, image capture sensors, or any other suitable sensors) could monitor the patient while sleeping and identify when the patient is not in REM sleep. If the patient is sleeping in a position that is not recommended for treating the patient's wound, the patient could be awakened when not in REM sleep and encouraged, or assisted, to move to a treatment position for further sleep.

Example Wound and Patient Characteristics

Figure 8:
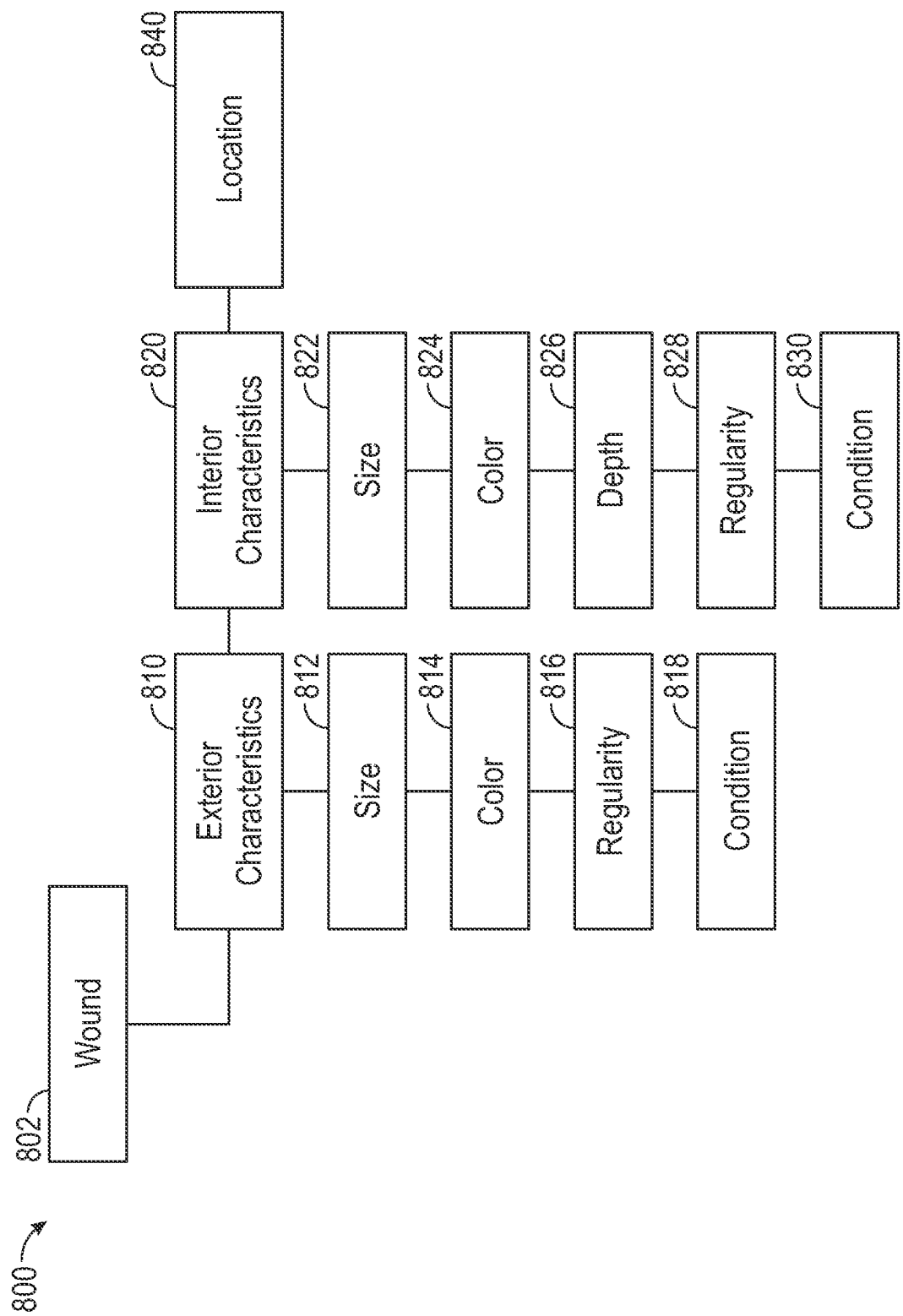
FIG. 8 depicts wound characteristics for use in predicting a wound care plan using an ML model, according to one embodiment.

FIG. 8 depicts example wound characteristics 800 for use in predicting a wound care plan using an ML model, according to one embodiment. In an embodiment, the wound characteristics 800 provide examples for the detected wound characteristics 702, illustrated in FIG. 7 and generated using a suitable wound detection ML model to detect characteristics from captured wound data (e.g., a captured wound image). For example, the wound characteristics 800 can include one or more wounds 802.

In an embodiment, each wound 802 includes exterior characteristics 810. The exterior characteristics 810 include size 812. For example, the size 812 can describe the exterior size of the wound 802 (e.g., the size of an area surrounding an open area of the wound or surrounding a more severely injured portion of the wound). In an embodiment, the size 812 can be described in area (e.g., $mm^2$), dimensions, perimeter circumference, or using any other suitable technique. For example, the size 812 can be expressed as a function describing the exterior size of the wound.

The exterior characteristics 810 can further include a color 814. For example, the color 814 can describe a color of the exterior portion of the wound. The color 814 can be an average color over the exterior area, a most extreme color over the exterior area (e.g., a darkest color, lightest color, color including the largest fraction of a particular shade, etc.), or any other suitable color. Further, the color 814 can be expressed using a numerical value, a tuple (e.g., a red, green, blue (RGB) value), a textual label, or using any other suitable technique.

In an embodiment, the exterior characteristics can further include a regularity 816 (e.g., a regularity of the shape of the wound), and a condition 818 (e.g., a condition of the exterior of the wound). For example, the condition 818 can describe whether the wound is dry or weeping, whether it is sutured or stapled, or any other suitable condition. These are merely examples, and the exterior characteristics 810 can include any suitable characteristics.

In an embodiment, the wound 802 further includes interior characteristics 820. The interior characteristics 820 include a size 822. For example, the size 812 can describe the interior size of the wound (e.g., the size of an open area of the wound or of a more severely injured portion of the wound). In an embodiment, the size 822 can be described in area (e.g., $mm^2$), dimensions, perimeter circumference, or using any other suitable technique. For example, the size 822 can be expressed as a function describing the interior size of the wound.

The interior characteristics 820 can further include a color 824. For example, the color 824 can describe a color of the interior portion of the wound. The color 824 can be an average color over the interior area, a most extreme color over the interior area (e.g., a darkest color, lightest color, color including the largest fraction of a particular shade, etc.), or any other suitable color. Further, the color 824 can be expressed using a numerical value, a tuple (e.g., a red, green, blue (RGB) value), a textual label, or using any other suitable technique.

The interior characteristics 820 can further include a depth 826. For example, the depth 826 can describe a depth of the wound. This can include a tissue depth for an open, or closed, wound, and can be expressed using a measurement (e.g., mm), relative to a surface portion of the skin, using a label, or using any other suitable technique. These are merely examples, and the interior characteristics 820 can include any suitable characteristics.

In an embodiment, the interior characteristics can further include a regularity 828 (e.g., a regularity of the shape of the wound), and a condition 830 (e.g., a condition of the interior of the wound). For example, the condition 830 can describe whether the wound is dry or weeping, whether it is sutured or stapled, or any other suitable condition.

In an embodiment, the wound 802 further includes a location 840. For example, the location 840 can describe the location of the wound on the patient's body. In an embodiment, the location 840 can be described relative to a portion of the patient's body, using a measurement system, or using any other suitable technique. The exterior characteristics 810, interior characteristics 820, and location 840 are merely examples, and the wound 802 can include any suitable characteristics, organized in any suitable manner.

Figure 9:
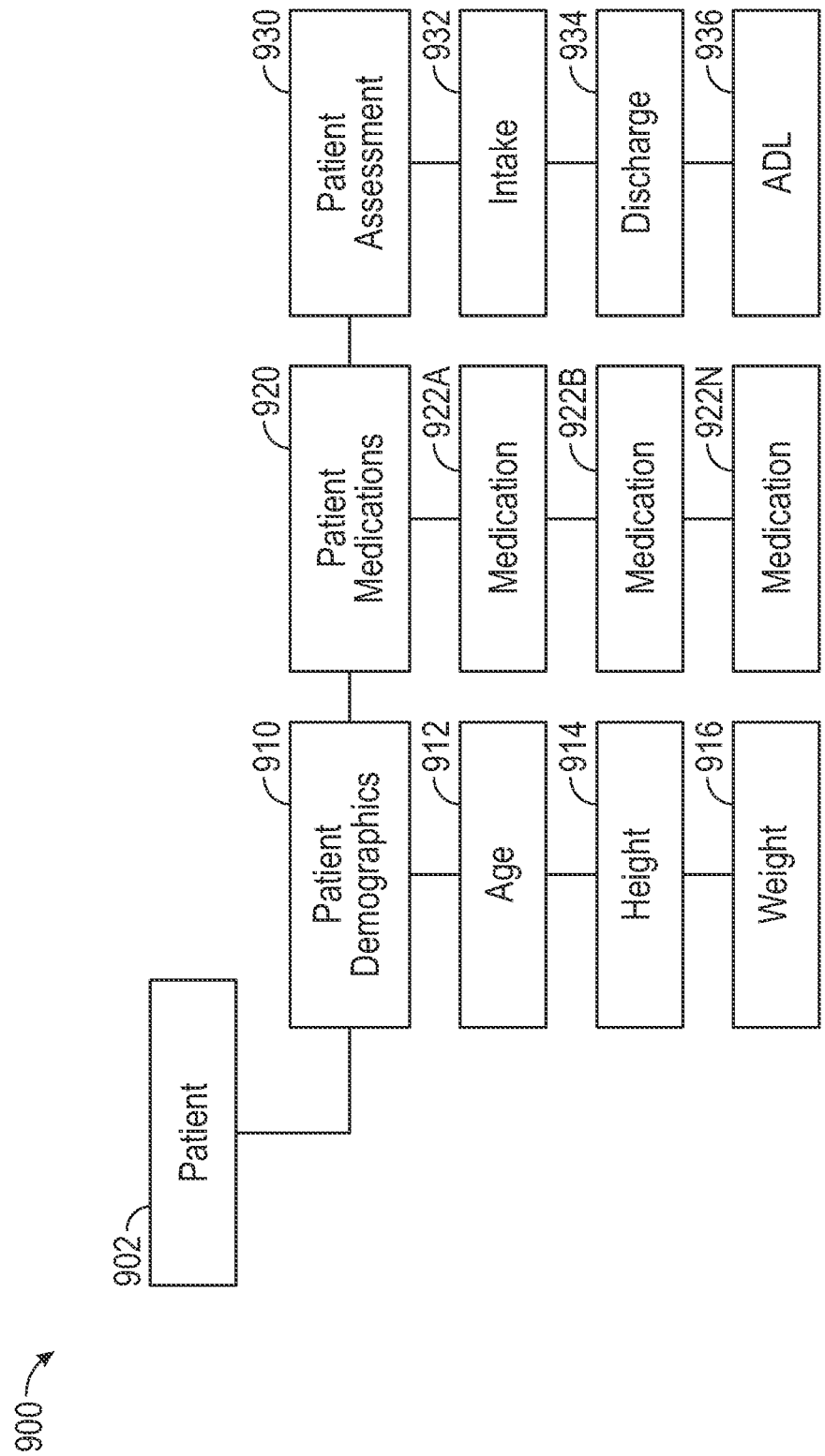
FIG. 9 depicts patient characteristics for use in predicting a wound care plan using an ML model, according to one embodiment.

FIG. 9 depicts patient characteristics 900 for use in predicting a wound care plan using an ML model, according to one embodiment. In an embodiment, the wound characteristics 900 provide examples for the patient characteristics 132, described above in relation to FIG. 1. A patient 902 includes patient demographics 910. For example, the patient demographics 910 can include age 912, height 914, and weight 916. These are merely examples, and the patient demographics 910 can include any suitable characteristics.

The patient 902 can further include patient medications 920. In an embodiment, the patient medications 920 include one or more medications 922A-N. These are merely examples, and the patient medications 920 can include any suitable data.

Further, the patient 902 can include one or more patient assessments 930 (e.g., a patient assessment 930 corresponding to each healthcare facility to which the patient has been admitted). In an embodiment, the patient assessment 930 includes an intake assessment 932. For example, an intake assessment can be performed for the patient upon intake to a healthcare facility (e.g., performed by a suitable healthcare professional, using a suitable automated assessment system, or both). The intake assessment can be memorialized as the intake assessment 932.

In an embodiment, the patient assessment 930 further includes a discharge assessment 934. For example, a discharge assessment can be performed for the patient upon discharge from a healthcare facility (e.g., performed by a suitable healthcare professional, using a suitable automated assessment system, or both). The discharge assessment can be memorialized as the discharge assessment 934.

The patient assessment 930 can further include an activities of daily living (ADL) assessment 936. For example, the ADL assessment can memorialize the patient's ability to dress, feed, ambulate, toilet, and perform their own hygiene. The ADL assessment can be memorialized as the ADL assessment 936. These are merely examples, and the patient assessment 930 can include any suitable data. Further, the patient demographics 910, patient medications 920, and patient assessment 930 are merely examples. The patient 902 can include any suitable patient data, organized in any suitable fashion.

Figure 10:
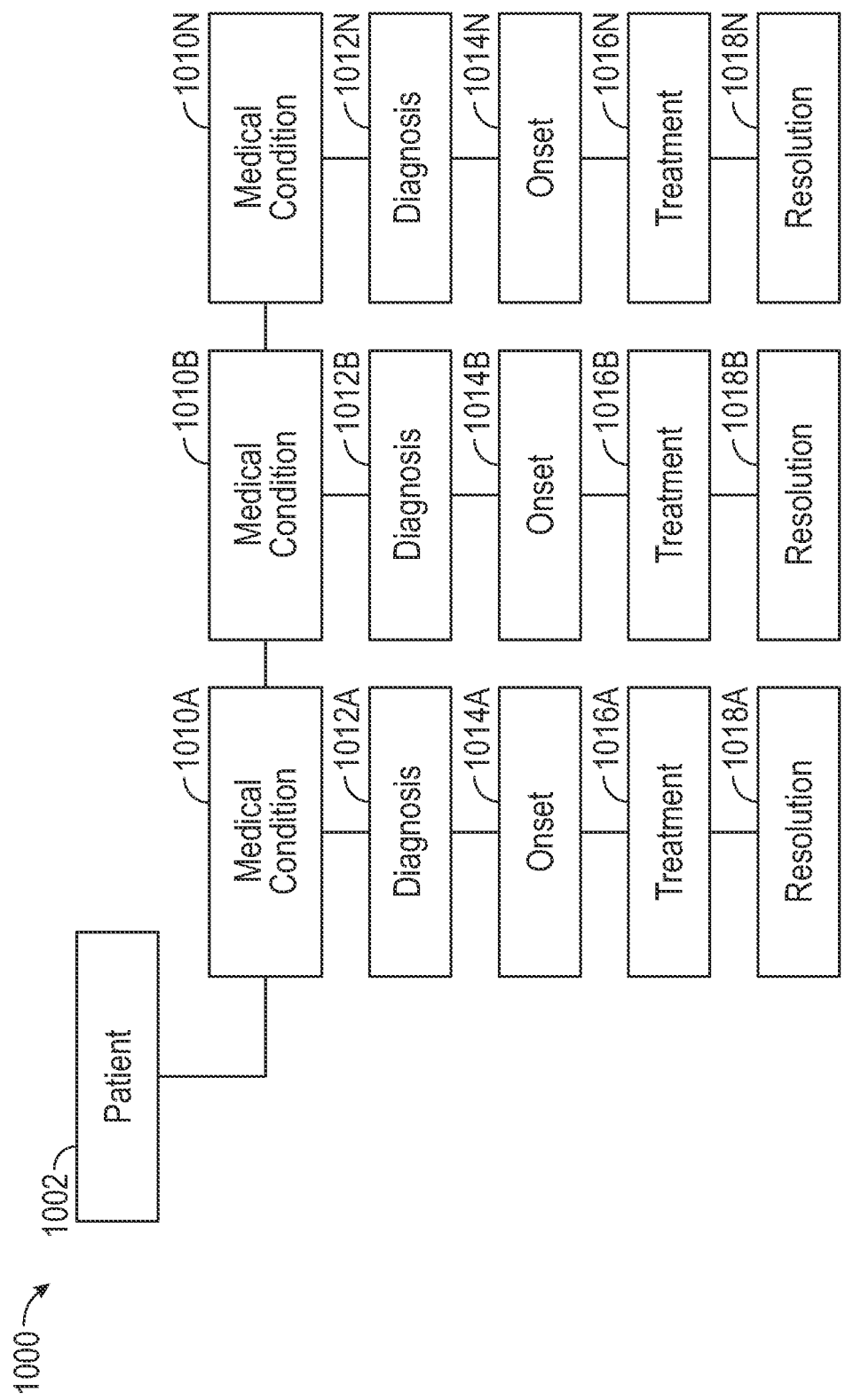
FIG. 10 depicts patient medical history for use in predicting a wound care plan using an ML model, according to one embodiment.

FIG. 10 depicts patient medical history 1000 for use in predicting a wound care plan using an ML model, according to one embodiment. In an embodiment, the patient medical history 1000 provide examples for the patient medical history 134, described above in relation to FIG. 1.

A patient 1002 includes one or more medical conditions 1010A-N. Each medical condition includes a respective diagnosis 1012A-N, a respective onset description 1014A-N (e.g., a date or textual description), a respective treatment 1016A-N (e.g., a treatment history for the medical condition), and a respective resolution 1018A-N (e.g., a date of resolution or a notation that the medical condition is ongoing). These are merely examples, and each medical condition 1010A-N can include any suitable data. Further, the medical conditions 1010A-N are merely examples, and the patient 1002 can include any suitable medical history data.

Figure 11:
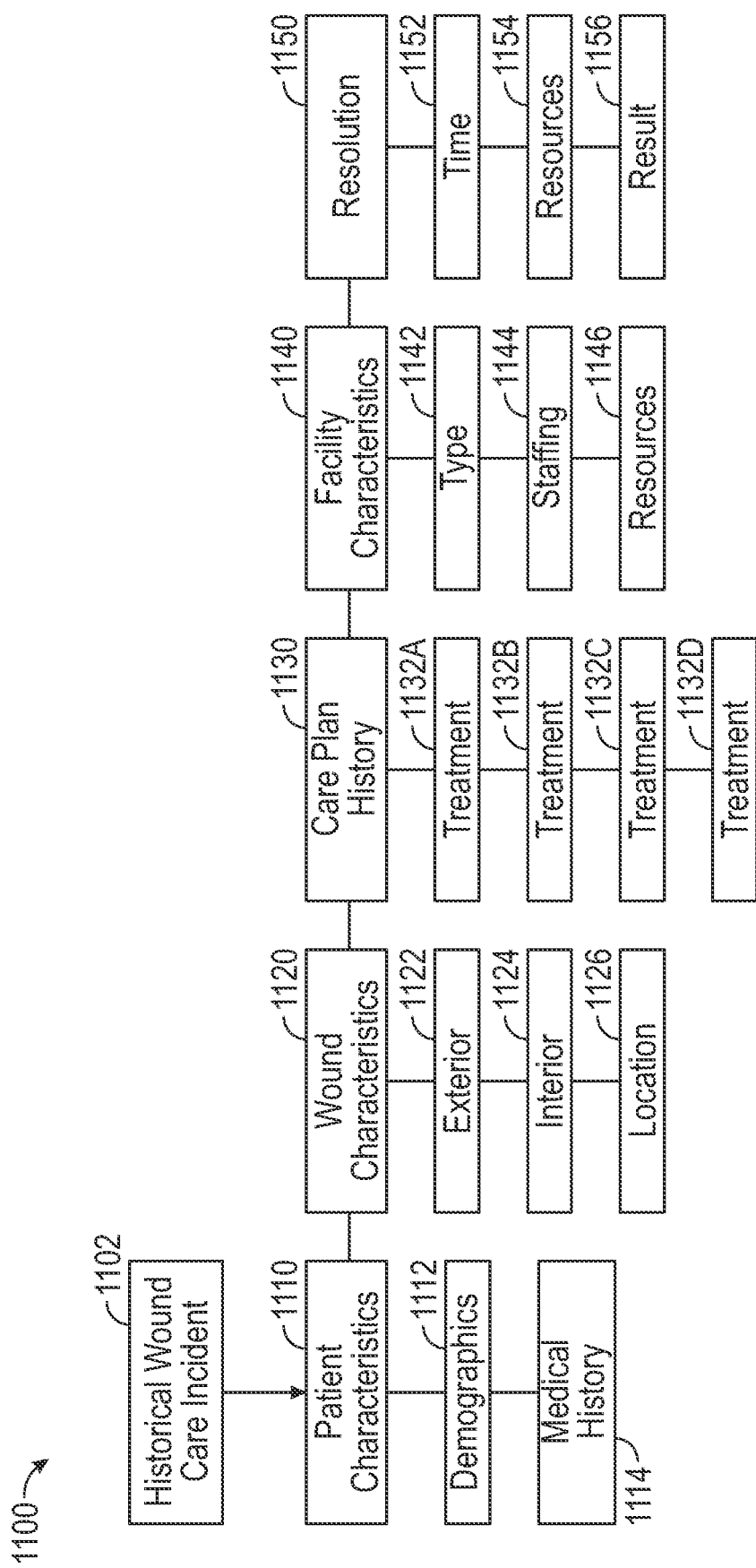
FIG. 11 depicts historical wound care incident data for use in predicting a wound care plan using an ML model, according to one embodiment.

FIG. 11 depicts historical wound care incident data 1100 for use in predicting a wound care plan using an ML model, according to one embodiment. In an embodiment, the historical wound care incident data 1100 provide examples for the historical wound care data 140, described above in relation to FIG. 1. Further, in an embodiment, the historical wound care incident data 1100 corresponds to any suitable patient (e.g., in addition to the patient for whom a wound is being treated). For example, the historical wound care incident data 1100 can be maintained by a healthcare provider (e.g., in a suitable anonymized or private format).

A historical wound care incident 1102 includes patient characteristics 1110. In an embodiment, the patient characteristics 1110 correspond with the patient characteristics 900 illustrated in FIG. 9 (e.g., for the patient with the historical wound). The patient characteristics 1110 include demographics 1112 (e.g., age, height, weight) and medical history 1114. These are merely examples, and the patient characteristics 1110 can include any suitable data.

The historical wound care incident 1102 further includes wound characteristics 1120. In an embodiment, the wound characteristics 1120 correspond with the wound characteristics 800 illustrated in FIG. 8 (e.g., for the relevant historical wound). The wound characteristics 1120 include exterior characteristics 1122 (e.g., size, color), interior characteristics 1124 (e.g., size, color, depth), and location 1126. These are merely examples, and the wound characteristics 1120 can include any suitable data.

The historical wound care incident 1102 further includes care plan history 1130. For example, the care plan history 1130 can describe one or more treatments 1132A-N used to treat the relevant wound. These are merely examples, and the care plan history 1130 can include any suitable data.

The historical wound care incident 1102 further includes one or more facility characteristics 1140 (e.g., describing any facilities used to treatment the wound, including outpatient and inpatient facilities). The facility characteristics 1140 include a type 1142 (e.g., inpatient, outpatient, or any other suitable type), staffing data 1144 (e.g., describing a number and type of staffing at the facility), and resources data 1146 (e.g., describing the available resources, including equipment, staffing, medication, and any other suitable resources). These are merely examples, and the facility characteristics 1140 can include any suitable data.

The historical wound care incident 1102 further includes a resolution 1150. For example, the resolution 1150 can include a time 1152 (e.g., a time of resolution), resources 1154 (e.g., equipment, staffing, and other resources used in resolution), and result 1156 (e.g., the end result of treatment). These are merely examples, and the resolution 1150 can include any suitable data. Further, the patient characteristics 1110, wound characteristics 1120, care plan history 1130, facility characteristics 1140, and resolution 1150, are merely examples. The historical wound care incident 1102 can include any suitable data.

Example of Training an ML Model for Predicting a Wound Care Plan

Figure 12:
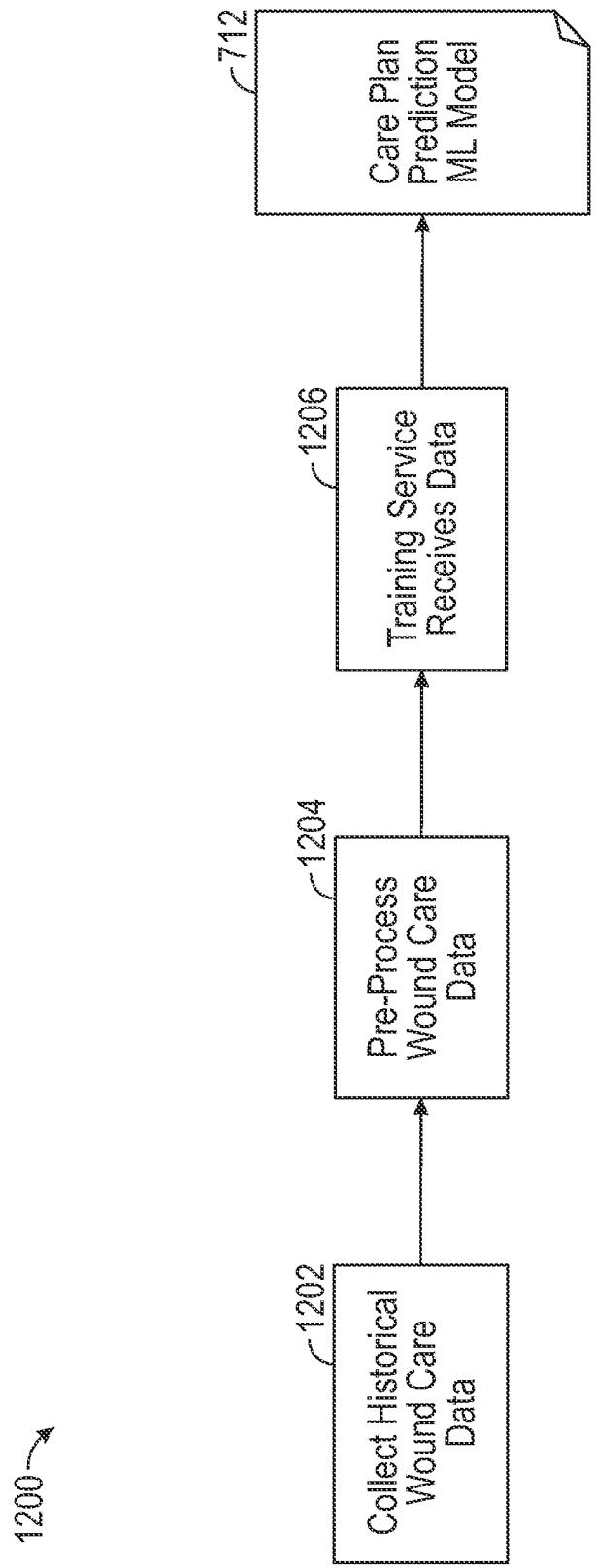
FIG. 12 is a flowchart illustrating training an ML model for wound management and treatment using computer vision, according to one embodiment.

FIG. 12 is a flowchart 1200 illustrating training an ML model for wound management and treatment using computer vision, according to one embodiment.

At block 1202, a training service (e.g., a human administrator or a software or hardware service) collects historical wound care data. For example, a wound prediction service (e.g., the wound prediction service 122 illustrated in FIGS. 1 and 2) can be configured to act as the training service and collect historical wound care data. This is merely an example, and any suitable software or hardware service can be used (e.g., a wound prediction training service).

At block 1204, the training service (or other suitable service) pre-processes the collected historical wound care data. For example, the training service can create feature vectors reflecting the values of various features, for each historical wound.

At block 1206, the training service receives the feature vectors and uses them to train a trained a care plan prediction ML model 712 (e.g., as discussed above in relation to FIG. 7).

In an embodiment, the pre-processing and training can be done as batch training. In this embodiment, all data is pre-processed at once (e.g., all historical wound image data and additional wound data), and provided to the training service at 1206. Alternatively, the pre-processing and training can be done in a streaming manner. In this embodiment, the data is streaming, and is continuously pre-processed and provided to the training service. For example, it can be desirable to take a streaming approach for scalability. The set of training data may be very large, so it may be desirable to pre-process the data, and provide it to the training service, in a streaming manner (e.g., to avoid computation and storage limitations).

Example of Using a Predicted Wound Care Plan

Figure 13:
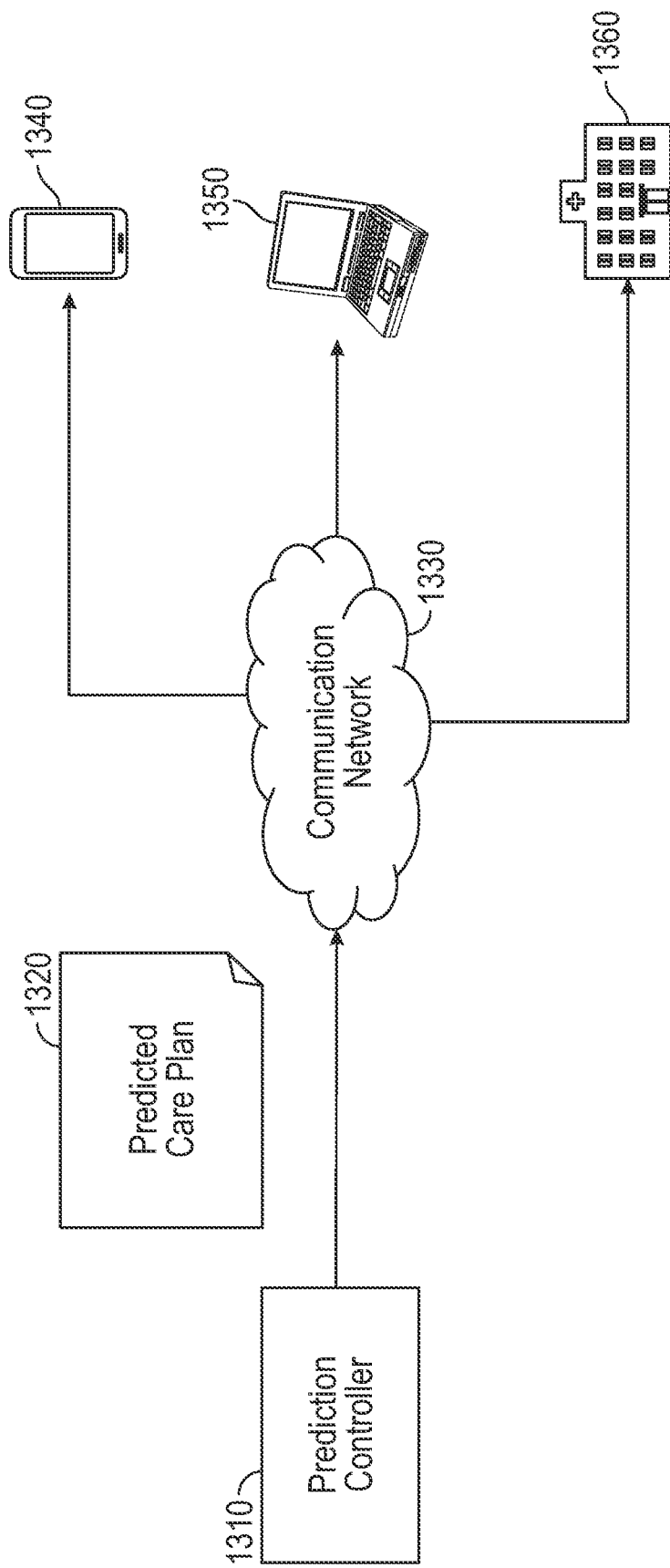
FIG. 13 depicts using a wound care plan generated using an ML model, according to one embodiment.

FIG. 13 depicts using a wound care plan generated using an ML model, according to one embodiment. In an embodiment, a prediction controller 1310 (e.g., the prediction controller 200 illustrated in FIG. 2) generates a predicted care plan 1320. For example, as discussed above in relation to block 310 in FIG. 3 and FIG. 7, a wound prediction service (e.g., the wound prediction service 122 illustrated in FIGS. 1-2) can use a wound prediction ML model (e.g., wound prediction ML model 124 illustrated in FIGS. 1-2) to predict a care plan.

For example, the wound prediction service can use detected wound characteristics, generated using a wound detection service (e.g., the wound detection service 112 illustrated in FIG. 1) and a wound detection ML model (e.g., the wound detection ML model 114 illustrated in FIGS. 1-2) from captured sensor data (e.g., a captured image of the wound). As discussed above, FIG. 8 provides an example of wound characteristics. The wound prediction service can further use any, or all, of patient characteristics (e.g., as illustrated in FIG. 9), patient medical history (e.g., as illustrated in FIG. 10), and historical wound care incidents (e.g., as illustrated in FIG. 11). In an embodiment, the wound prediction service uses the historical wound care data for ongoing training of the wound detection ML model. Alternatively, the wound prediction service does not receive the historical wound care data.

In an embodiment, the prediction controller 1310 transmits the predicted care plan 1320 over a communication network 1330 to any, or all, of a patient 1340, a care provider 1350, and a healthcare facility 1360. The communication network 1330 can be any suitable communication network, including the Internet, a wide area network, a local area network, or a cellular network, and can use any suitable wired or wireless communication technique (e.g., WiFi or cellular communication).

In an embodiment, any, or all, of the patient 1340, the care provider 1350, and the healthcare facility 1360 receive the predicted care plan. The predicted care plan 1320 can then be used to treat the patient wound. For example, the patient 1340 can receive the predicted care plan 1320 at a suitable electronic device (e.g., a smartphone, tablet, laptop computer, desktop computer, or any other suitable device) and can use it for treatment (e.g., using a mobile application or local application running on the patient device, or accessing the predicted care plan 1320 over the communication network 1330).

Similarly, the care provider 1350 or the healthcare facility 1360 (e.g., a healthcare professional at the healthcare facility 1360) can receive the predicted care plan 1320. In an embodiment, any, or all, of patient 1340, the care provider 1350, and the healthcare facility 1360 store the predicted care plan 1320. For example, this can allow the recipient to access the predicted care plan 1320 without requiring a continuous network connection.

Figure 14:
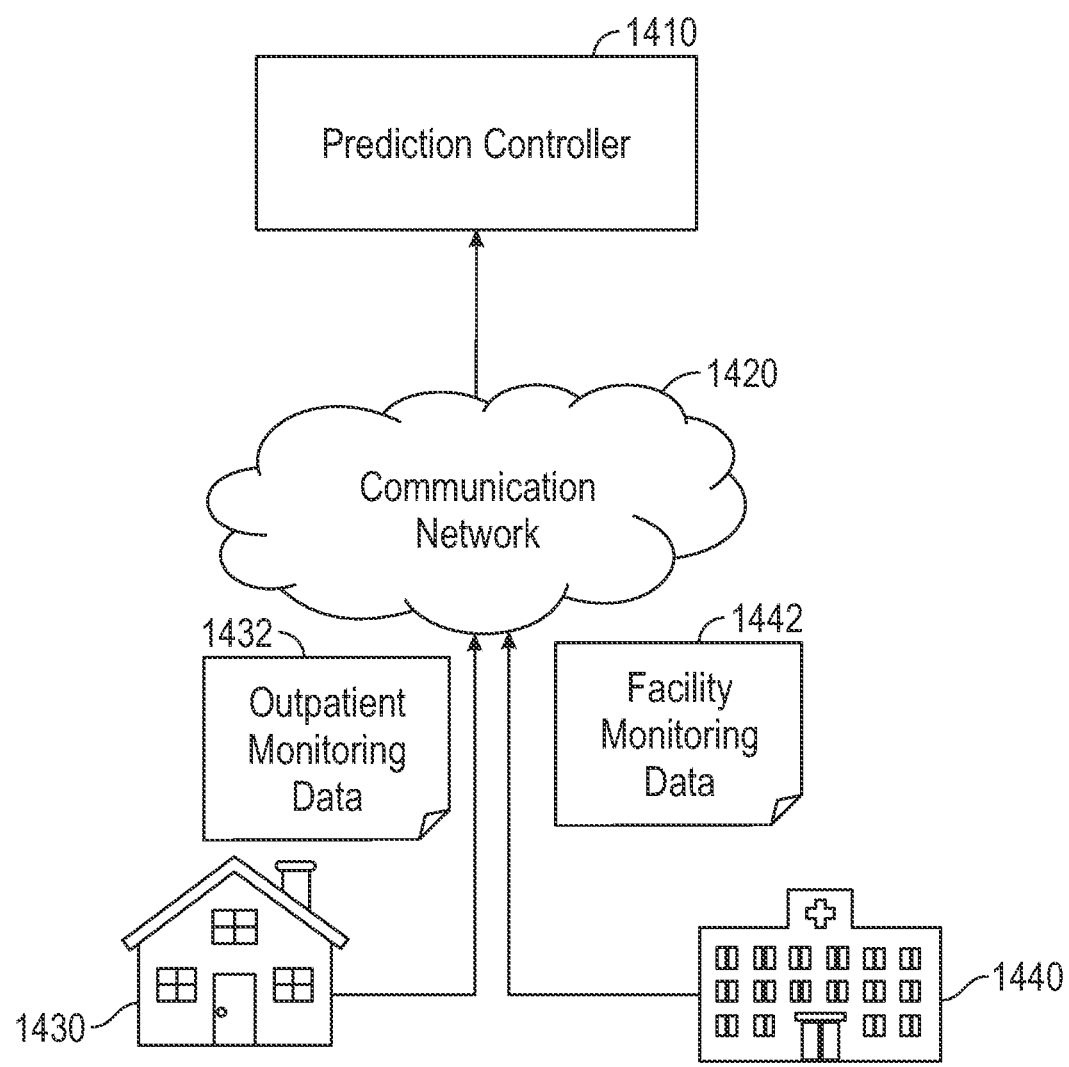
FIG. 14 depicts ongoing monitoring of patient care for wound management and treatment using computer vision, according to one embodiment.

FIG. 14 depicts ongoing monitoring of patient care for wound management and treatment using computer vision, according to one embodiment. As discussed above in relation to the ongoing patient monitoring data 170 illustrated in FIG. 1, in an embodiment the patient care plan can be revised based on ongoing monitoring of the treatment progress for the patient's wound. In an embodiment, a patient is treated at an outpatient facility 1430. The outpatient facility 1430 continues to monitor treatment of the wound.

For example, the patient, or a care provider, can continue to capture electronic images of the wound as it is treated, or capture electronic sensor data during treatment. The patient, or care provider, can transmit this outpatient monitoring data 1432 (e.g., the captured image or other sensor data) to a prediction controller 1410 (e.g., the prediction controller 200 illustrated in FIG. 2) using a communication network 1420. The communication network 1420 can be any suitable communication network, including the Internet, a wide area network, a local area network, or a cellular network, and can use any suitable wired or wireless communication technique (e.g., WiFi or cellular communication).

In an embodiment, the prediction controller 1410 can use the outpatient monitoring data 1432 to revise the predicted care plan. For example, as discussed above in relation to FIG. 4, a computer vision service can use a computer vision ML model to identify wound characteristics from a captured wound image. These wound characteristics can then be used to predict a wound care plan using a care plan prediction ML model (e.g., as discussed above in relation to FIG. 7). The outpatient monitoring data 1432 can include one or more additional captured images of the wound, and a suitable computer vision ML model can be used to detect wound characteristics from these images. The prediction controller 1410 can then use the updated wound characteristics to predict an updated wound care plan.

Alternatively, or in addition, the patient is treated at healthcare facility 1440. Just like at the outpatient facility 1430, the patient's wound can be continuously monitored at the healthcare facility 1440 (e.g., by a care provider or by the patient). The care provider, or patient, can transmit facility monitoring data 1442 (e.g., updated captured sensor data for the wound to the prediction controller 1410 using the communication network 1420. The prediction controller 1410 can use the facility monitoring data 1442 to revise the predicted care plan. For example, as discussed above in relation to FIG. 4, a computer vision service can use a computer vision ML model to identify wound characteristics from a captured wound image. These wound characteristics can then be used to predict a wound care plan using a care plan prediction ML model (e.g., as discussed above in relation to FIG. 7). The facility monitoring data 1442 can include one or more additional captured images of the wound, and a suitable computer vision ML model can be used to detect wound characteristics from these images. The prediction controller 1410 can then use the updated wound characteristics to predict an updated wound care plan.

Further, in an embodiment, the outpatient monitoring data 1432 and the facility monitoring data 1442 can be used to continuously train the care plan prediction ML model. For example, outpatient monitoring data 1432 and the facility monitoring data 1442 can include additional captured images of the wound during treatment. The computer vision service can be used to identify characteristics of these wounds, and the prediction ML model can identify, from these characteristics, how treatment is progressing for the patient. This indication of progress, along with the previously predicted care plan, can be used as training data to further refine the care plan prediction ML model.

Example Clauses

Implementation examples are described in the following numbered clauses:

Clause 1: A method, comprising: determining a plurality of characteristics of a wound for a patient based on an image of the wound, comprising: detecting the plurality of characteristics based on analyzing the image using a first machine learning (ML) model trained to detect wound characteristics from a captured image, identifying patient medical data comprising a plurality of characteristics relating to a medical history for the patient, and predicting a first care plan for the patient based on providing the plurality of characteristics of the wound and the patient medical data to a second ML model, wherein the second ML model is trained to predict the first care plan using prior wound care outcome data comprising a plurality of prior wound care outcomes relating to a plurality of prior patients, and wherein the first care plan is configured to be used to treat the wound for the patient.

Clause 2: The method of any of clauses 1 or 3-10, further comprising: determining a second plurality of characteristics of the wound for the patient based on analyzing a second image of the wound, captured during treatment of the wound relating to the predicted first care plan, using the first ML model, and predicting a second care plan for the patient based on providing the second plurality of characteristics of the wound to the second ML model.

Clause 3: The method of any of clauses 1-2 or 4-10, wherein the second plurality of characteristics of the wound is further used to modify the second ML model through further training based on the second plurality of characteristics and the first care plan.

Clause 4: The method of any of clauses 1-3 or 5-10, further comprising: identifying a prophylactic treatment task for the wound based on at least one of the plurality of characteristics of the wound or the care plan, and transmitting an electronic alert relating to the treatment task.

Clause 5: The method of any of clauses 1-4 or 6-10, wherein identifying the prophylactic treatment task is based on the at least one of the plurality of characteristics of the wound and is identified using the second ML model, further comprising: transmitting the alert to a care provider for the patient electronically using a communication network, prior to completing the predicting the care plan for the patient.

Clause 6: The method of any of clauses 1-5 or 7-10, wherein detecting the plurality of characteristics of the wound further comprises: determining at least one of a depth, a color, or a size of the wound, based on the image of the wound.

Clause 7: The method of any of clauses 1-6 or 8-10, wherein the prior wound care outcome data comprises data reflecting wound characteristics, treatment, and resolution for each of a plurality of past wounds relating to the plurality of prior patients.

Clause 8: The method of any of clauses 1-7 or 9-10, wherein the care plan comprises one or more recommended treatment tasks for the wound, comprising at least one of: a medication, a patient action, or a care provider action to treat the wound.

Clause 9: The method of any of clauses 1-8 or 10, further comprising: modifying treatment of the wound based on the one or more recommended treatment tasks.

Clause 10: The method of any of clauses 1-9, further comprising: identifying additional data captured by a sensor during treatment or assessment of the wound, wherein predicting the first care plan is further based on providing the identified additional data to the second ML model.

Clause 11: A processing system, comprising: a memory comprising computer-executable instructions; and one or more processors configured to execute the computer-executable instructions and cause the processing system to perform a method in accordance with any one of Clauses 1-10.

Clause 12: A processing system, comprising means for performing a method in accordance with any one of Clauses 1-10.

Clause 13: A non-transitory computer-readable medium comprising computer-executable instructions that, when executed by one or more processors of a processing system, cause the processing system to perform a method in accordance with any one of Clauses 1-10.

Clause 14: A computer program product embodied on a computer-readable storage medium comprising code for performing a method in accordance with any one of Clauses 1-10.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method, comprising:
    determining a plurality of characteristics of a wound for a patient based on an image of the wound, comprising:
        detecting the plurality of characteristics based on analyzing the image using a first machine learning (ML) model;
    identifying patient medical data comprising a plurality of characteristics relating to a medical history for the patient;
    predicting a first care plan for the patient based on providing both: (i) the plurality of characteristics of the wound detected based on analyzing the image using the first ML model and (ii) the patient medical data, to a second ML model different from the first ML model, wherein the first care plan is configured to be used to treat the wound for the patient;
    identifying a prophylactic treatment task for the wound based on at least one of the plurality of characteristics of the wound or the care plan; and
    transmitting an electronic alert relating to the treatment task.

2. The method of claim 1, wherein identifying the prophylactic treatment task is based on the at least one of the plurality of characteristics of the wound and is identified using the second ML model, further comprising:
    transmitting the alert to a care provider for the patient electronically using a communication network, prior to completing the predicting the care plan for the patient.

3. A method, comprising:
    determining a plurality of characteristics of a wound for a patient based on an image of the wound, comprising:
        detecting the plurality of characteristics based on analyzing the image using a first machine learning (ML) model;
    identifying patient medical data comprising a plurality of characteristics relating to a medical history for the patient; and
    predicting a first care plan for the patient based on providing both: (i) the plurality of characteristics of the wound detected based on analyzing the image using the first ML model and (ii) the patient medical data, to a second ML model different from the first ML model, wherein the first care plan is configured to be used to treat the wound for the patient.

4. The method of claim 3, further comprising:
    determining a second plurality of characteristics of the wound for the patient based on analyzing a second image of the wound, captured during treatment of the wound relating to the predicted first care plan, using the first ML model; and
    predicting a second care plan for the patient, different from the first care plan for the patient, based on providing the second plurality of characteristics of the wound to the second ML model,
        wherein the second ML model predicts the different second care plan for the patient based on one or more differences between the second plurality of characteristics of the wound and the plurality of characteristics of the wound.

5. The method of claim 4, wherein the second plurality of characteristics of the wound is further used to modify the second ML model through further training based on the second plurality of characteristics and the first care plan.

6. The method of claim 3, further comprising:
    identifying a prophylactic treatment task for the wound based on at least one of the plurality of characteristics of the wound or the care plan.

7. The method of claim 3, wherein detecting the plurality of characteristics of the wound further comprises:
    determining at least one of a depth, a color, or a size of the wound, based on the image of the wound.

8. The method of claim 3, wherein the second ML model is trained using prior wound care outcome data comprising data reflecting wound characteristics, treatment, and resolution for each of a plurality of past wounds relating to a plurality of prior patients.

9. The method of claim 3, further comprising:
    identifying additional data captured by a sensor during treatment or assessment of the wound,
        wherein predicting the first care plan is further based on providing the identified additional data to the second ML model.

10. The method of claim 3, wherein the care plan comprises one or more recommended treatment tasks for the wound, comprising at least one of: a medication, a patient action, or a care provider action to treat the wound.

11. The method of claim 10, further comprising:
    modifying treatment of the wound based on the one or more recommended treatment tasks.

12. An apparatus comprising:
    a memory; and a hardware processor communicatively coupled to the memory, the hardware processor configured to perform operations comprising:
   determining a first plurality of characteristics of a wound for a patient based on an image of the wound, comprising:
      detecting the first plurality of characteristics based on analyzing the image using a first machine learning (ML) model;
   identifying patient medical data comprising a plurality of characteristics relating to a medical history for the patient;
   predicting a first care plan for the patient based on providing both: (i) the first plurality of characteristics of the wound detected based on analyzing the image using the first ML model and (ii) the patient medical data, to a second ML model different from the first ML model,
      wherein the first care plan is configured to be used to treat the wound for the patient,
   determining a second plurality of characteristics of the wound for the patient based on analyzing a second image of the wound, captured during treatment of the wound relating to the predicted first care plan, using the first ML model; and
   predicting a second care plan for the patient, different from the first care plan for the patient, based on providing the second plurality of characteristics of the wound to the second ML model,
      wherein the second ML model predicts the different second care plan for the patient based on one or more differences between the second plurality of characteristics of the wound and the plurality of characteristics of the wound.

13. The apparatus of claim 12, wherein the second plurality of characteristics of the wound is further used to modify the second ML model through further training based on the second plurality of characteristics and the first care plan.

14. The apparatus of claim 12, the operations further comprising:
   identifying a prophylactic treatment task for the wound based on at least one of the plurality of characteristics of the wound or the care plan; and
   transmitting an electronic alert relating to the treatment task.

15. The apparatus of claim 14, wherein identifying the prophylactic treatment task is based on the at least one of the plurality of characteristics of the wound and is identified using the second ML model, the operations further comprising:
   transmitting the alert to a care provider for the patient electronically using a communication network, prior to completing the predicting the care plan for the patient.

16. The apparatus of claim 12, wherein the second ML model is trained using prior wound care outcome data comprising data reflecting wound characteristics, treatment, and resolution for each of a plurality of past wounds relating to a plurality of prior patients.

17. A non-transitory computer-readable medium comprising instructions that, when executed by a processor, cause the processor to perform operations comprising:
   determining a first plurality of characteristics of a wound for a patient based on an image of the wound, comprising:
      detecting the first plurality of characteristics based on analyzing the image using a first machine learning (ML) model;
   identifying patient medical data comprising a plurality of characteristics relating to a medical history for the patient;
   predicting a first care plan for the patient based on providing both: (i) the first plurality of characteristics of the wound detected based on analyzing the image using the first ML model and (ii) the patient medical data, to a second ML model different from the first ML model,
      wherein the first care plan is configured to be used to treat the wound for the patient,
   determining a second plurality of characteristics of the wound for the patient based on analyzing a second image of the wound, captured during treatment of the wound relating to the predicted first care plan, using the first ML model; and
   predicting a second care plan for the patient, different from the first care plan for the patient, based on providing the second plurality of characteristics of the wound to the second ML model,
      wherein the second ML model predicts the different second care plan for the patient based on one or more differences between the second plurality of characteristics of the wound and the plurality of characteristics of the wound.

18. The non-transitory computer-readable medium of claim 17,
   wherein the second plurality of characteristics of the wound is further used to modify the second ML model through further training based on the second plurality of characteristics and the first care plan.

19. The non-transitory computer-readable medium of claim 17, the operations further comprising:
   identifying a prophylactic treatment task for the wound based on the plurality of characteristics of the wound, using the second ML model; and
   transmitting an electronic alert to a care provider for the patient electronically using a communication network, prior to completing the predicting the care plan for the patient.

20. The non-transitory computer-readable medium of claim 17, wherein the second ML model is trained using prior wound care outcome data comprising data reflecting wound characteristics, treatment, and resolution for each of a plurality of past wounds relating to a plurality of prior patients.

* * * * *